US006013782A

United States Patent [19]
Dedhar et al.

[11] Patent Number: 6,013,782
[45] Date of Patent: Jan. 11, 2000

[54] INTEGRIN-LINKED KINASE AND ITS USES

[75] Inventors: Shoukat Dedhar, Vancouver; Greg Hannigan, Ontario, both of Canada

[73] Assignee: Sunnybrook Health Sciences Center, Ontario, Canada

[21] Appl. No.: 08/955,841

[22] Filed: Oct. 21, 1997

Related U.S. Application Data

[63] Continuation-in-part of application No. 08/752,345, Nov. 19, 1996, abandoned
[60] Provisional application No. 60/009,074, Dec. 21, 1995.
[51] Int. Cl.$^7$ .......................... C07H 21/02; C12N 15/00; C12P 21/04
[52] U.S. Cl. .................... 536/23.1; 536/23.1; 435/320.1; 435/325; 435/70.1
[58] Field of Search ........................ 536/23.1; 435/320.1; 800/8

[56] References Cited

FOREIGN PATENT DOCUMENTS

| 96/00760 | 5/1996 | Canada . |
| WO94/21781 | 9/1974 | WIPO . |
| WO96/36642 | 11/1996 | WIPO . |

OTHER PUBLICATIONS

V.G. Pursel et al. J. Reprod. Fert., Suppl. 40, 235–245, 1990.
Catherine A. Kappel et al. Current Opinion in Biotechnology, 3:548–553, 1992.
L. Hillier et al. GenBank H70160 and R91874, Oct. 1995.
Palmiter et al., Science 222:809–814, Nov. 1983.
X. Jacq et al. Cell 79 (1), 107–117, 1994.
86$^{th}$ Annual Meeting of the American Association for Cancer Research, Mar. 1995 p. 361, XP000673939, Hannigan et al. "Cloning of a novel protein kinase associated with beta 1 integrin cytoplasmic tails".
Molecular Biology of the Cell, vol. 6, supl. Nov. 1995 p. 2244 XP000673935, Hannigan et al., "Overexpression of a novel integrin linked kinase (ILK) induces a transformed phenotype and cyclin D1 expression".
Morino et al. (1995) J. Biological Chemistry 270:269–273, "Matrix–integrin interaction activates the mitogen–activated protein kinase, p44erk–1 and p42erk–2".
Genbank accession No. H70160.
Dedhar and Hannigan (1996) Curr. Opin. Cell Bio. 8:657–559, "Integrin cytoplasmic interactions and bidirectional transmembrane signalling".
Hannigan et al. (1996) Nature 379:91–96, Regulation of Cell Adhesion and Anchorage Dependent growth by a new beta 1–integrin linked protein kinase.

*Primary Examiner*—Bruce R. Campell
*Assistant Examiner*—Shin-Lin Chen
*Attorney, Agent, or Firm*—Pamela Sherwood; Bozicevic, Field & Francis

[57] ABSTRACT

Methods for isolating ILK genes are provided. The ILK nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

6 Claims, 23 Drawing Sheets

```
gaattcatctgtcgactgctactaccacgggagttcccgagaaggatcctgcagcccgagt      60
cccgaggataaagcttggggttcatcctcctgatcactccacagtcctcaggct           120
tccccaatccaggggactcggcgccggacgctgtaTGGACGACATTTCACTCAGTGC         180
                              M  D  D  I  F  T  Q  C             8
CGGGAGGGCAACGCAGTCGCCGTTCGCCTGTGGCTGGACAACGGAGAACGACCTCAAC        240
 R  E  G  N  A  V  R  L  W  L  D  N  T  E  N  D  L  N            28
CAGGGGGACGATCATGGGCTTCTCCCCTTGCCACTGGGCCTGCCGAGAGGGCCGCTCTGCT     300
 Q  G  D  D  H  G  F  S  P  L  H  W  A  C  R  E  G  R  S  A      48
GTGGTTGAGATGTTGATCATGCGGGGCACGAGATCAATGAACCGTGGGGATGAC           360
 V  V  E  M  L  I  M  R  G  A  R  I  N  V  M  N  R  G  D  D      68
ACCCCCCTGCATCTGGCCAGCCAGTCATGGACACCGTGATATTGTACAGAAGCTATTGCAG    420
 T  P  L  H  L  A  A  S  H  G  H  R  D  I  V  Q  K  L  L  Q      88
TACAAGGCAGACATCAATGCAGTGAATGAACACGGGAATGTGCCCACTATGCCTGT         480
 Y  K  A  D  I  N  A  V  N  E  H  G  N  V  P  L  H  Y  A  C     108
TTTGGGGGCCAAGATCAAGTGGCCAGAGGACCTGGTTGCCAATGGGCCCTTGTCAGCATC    540
 F  W  G  Q  D  Q  V  A  E  D  L  V  A  N  G  A  L  V  S  I     128
TGTAACAAGTATGGAGAGATGCCCTGTGGACACCCCTGAGAGAGCTTCTC               600
```

Fig. 1a (continued on page 2/23)

```
  C  N  K  Y  G  E  M  P  V  D  K  A  K  A  P  L  R  E  L  L          148
CGAGAGCGGGGCAGAGAAGATGGGCCAGAATCTCAACCGTATTCCATACAAGGACACATTC         660
  R  E  R  A  E  K  M  G  Q  N  L  N  R  I  P  Y  K  D  T  F          168
TGGAAGGGGACCACCCGCACTCGGCCCCGAAATGGAACCCTGAACAACACTCTGGCATT          720
  W  K  G  T  T  R  T  R  P  R  N  G  T  L  N  K  H  S  G  I          188
GACTTCAAACAGCTTAACTTCCTGACGAAGCTCAACGAGAATCACTCTGGAGAGCTATGG         780
  D  F  K  Q  L  N  F  L  T  K  L  N  E  N  H  S  G  E  L  W          208
AAGGGCCCGCTGGCCAGGGCAATGACATTGTCGTGAAGGTGCTGAGACTTCGAGACTGGAGT       840
  K  G  R  W  Q  G  N  D  I  V  V  K  V  L  K  V  R  D  W  S          228
ACAAGGAAGAGCAGGGACTTCAATGAAGAGTGTCCCCGGCTCCGGCTCAGGATTTTCTCGCATCCA   900
  T  R  K  S  R  D  F  N  E  E  C  P  R  L  R  I  F  S  H  P          248
AATGTGCTCCCCAGTGCTGCCAGTCCTCCAGTCCTGCCACCTACTCCTCATCCTACTCTCATC     960
  N  V  L  P  V  L  G  A  C  Q  S  P  P  A  P  H  P  T  L  I          268
ACACACTGGATGCCGTATGGAATCCCTCTACAATGTACTACATGAAGGCACCAATTTCGTC        1020
  T  H  W  M  P  Y  G  S  L  Y  N  V  L  H  E  G  T  N  F  V          288
GTGGACCAGAGCCAGGCTGTGAAGTTTGCTTTGGACATGGCAAGGGGCATGGCCTTCCTA         1080
  V  D  Q  S  Q  A  V  K  F  A  L  D  M  A  R  G  M  A  F  L          308
CACACACTAGAGCCCCTCATCCCACGACATGCACTCAATAGCCCGTAGTGTAATGATTGAT       1140
  H  T  L  E  P  L  I  P  R  H  A  L  N  S  R  S  V  M  I  D          328
```

Fig. 1a (continued on page 3/23)

```
GAGGACATGACTGCCCGAATTAGCAGCATGGCTGATGTGTCAAGTTCTCTTTCCAATGTCCTGGT    1200
 E  D  M  T  A  R  I  S  M  A  D  V  K  F  S  F  Q  C  P  G           348
CGCATGTATGCACCTGCTGGGTAGCCCCGAAGCTCTGCAGAAGAAGCCTGAAGACACA            1260
 R  M  Y  A  P  A  W  V  A  P  E  A  L  Q  K  K  P  E  D  T           368
AACAGACGCTCAGCAGACAGTGGAGTTTGCAGTGCTTCTGTGGGAACTGGTGACACGG            1320
 N  R  R  S  A  D  M  W  S  F  A  V  L  L  W  E  L  V  T  R           388
GAGGTACCCTTTGCTGACCTCTCCAATATGGAGATTGGAATGAAGGTGGCATTGGAAGGC          1380
 E  V  P  F  A  D  L  S  N  M  E  I  G  M  K  V  A  L  E  G           408
CTTCGGCCTACCATCCCACCAGGTATTCCCCTCATGTGTAAGCTCATGAAGATCTGC             1440
 L  R  P  T  I  P  P  G  I  S  P  H  V  C  K  L  M  K  I  C           428
ATGAATGAAGACCCTGCAAAGCGACCCAAATTTGACATGATTGTGCCTATCCTTGAGAAG          1500
 M  N  E  D  P  A  K  R  P  K  F  D  M  I  V  P  I  L  E  K           448
ATGCAGGACAAGtaggactggaaggtccctgcctgaactccagaggtgtcgggacatggt          1560
 M  Q  D  K  *
tggggaatgcacctcccccaaagcagcaggcctctggttgcctccccccgcctccagtcat         1620
ggtactacccccagcctggggtccatcccctcccccataccactgtgcgcaagagg              1680
ggcgggctcagagtttgtcacttgccacactggtgtctccaacatgggagggatcagcc          1740
ccgcctgtcacaataaagtttattatgaaaaaaaaaaaaaaaaa                          1789
```

FIGURE 1A

```
                 I                                              II
Csk    .NMKELKLLQ TIGKGEFGDV MLGDYRGN.K VAVKCIKNDA .TAQ....AF
Yes    IPRESLREV  KLGQGCFGEV WMGTWNGTTK VAIKTLKPGT MMPEAFLQ..
Ctrl   IPWCDLNIKE KIGAGSFGTV HRAEWHGS.D VAVKILMEQD FHAE.RVNEF    235
B-raf  IPDGQITVGQ RIGSGSFGTV YKGKWHG..D VAVKMLNVTA PTPQQ.LQAF
Ilk    IDFKQLNFLT KLNENHSGEL WKGRWQGN.D IVVKVLDKVR DWSTRKSRDF III               IV                              V
Csk    LAEASVMTQ  LRHSNLVQLL GVIVEE.KGG LYIVTEYMAK GSLVDYLRSR
Yes    ..EAQIMKK  LRHDKLVPLY AVVSEE...P IYIVTEFMTK GSLLDFLKEG
Ctrl   LREVAIMKR  LRHPNIVLFM GAVTQPP..N LSIVTEYLSR GSLYRLLHKS    283
B-raf  KNEVGVLRK  TRHVNILLFM GYSTKP...Q LAIVTQWCEG SSLYHHLHII
Ilk    NEECPRLRI  FSHPNVLPVL GACQSPPAPH PTLITHWMPY GSLYNVLHE.

VIa                           VIb
Csk    GRSV.LGGDC LLKFSLDVCE AMEYLEGN.. .NFVHRDLAA RNVLVS.E
Yes    EGKF.LKLPQ LVDMAAQIAD GMAYIERM.. .NYIHRDLRA ANILVG.D
Ctrl   GAREQLDERR RLSMAYDVAK GMNYLH.NRN PPIVHRDLKS PNLLV.DK      329
B-raf  ETKFEMI..K LIDIARQTAQ GMDYLHAK.. .SIIHRDLKS NNIFLH.E
Ilk    GTNFVVDQSQ AVKFALDMAR GMAFLH.TLE PLIPRHALNS RSVMI.DE
```

Fig. 1b (continued on page 5/23)

|       | VII        |            |            |            |            |     |
|-------|------------|------------|------------|------------|------------|-----|
| Csk   | DNVAKVSDFG | LTK.....EA | SSTQDTGKLP | VKWTAPEALR | ...EKKFSTK |     |
| Yes   | NLVCKIADFG | LARLIED.NE | YTARQGAKFP | IKWTAPEAAL | ...YGRFTIK |     |
| Ctrl  | KYTVKVCDFG | LSRLKAS.TF | LSSKSAAGTP | .EWMAPEVLR | ...DEPSNEK |     |
| B-raf | DLTVKIGDFG | LATVKSRWSG | SHQFEQLSGS | ILWMAPEVIR | MQDKNPYSFQ |     |
| Ilk   | DMTARIS... | MADVKFSFQC | PGRM.YA..P | .AWVAPEALQ | KKPEDTNRSS | 372 |

|       | IX         |            |            | X          |            |     |
|-------|------------|------------|------------|------------|------------|-----|
| Csk   | SDVWSFGILL | WEIYSFGRVP | YPRIPLKD.V | VPRVEKGY.. | KMDAPDGCPP |     |
| Yes   | SDVWSFGILL | TELVTKGRVP | YPGMVNRE.V | LEQVERGY.. | RMPCPQGCPE |     |
| Ctrl  | SDVYSFGVIL | WELAT.LQQP | WGNL.NPAQV | VAAVGFKCK. | RLEIPRNLNP |     |
| B-raf | SDVYAFGIVL | YELMT.GQLP | YSNINNRDQI | IFMVGRGYLS | PDLSKVRSNC |     |
| Ilk   | ADMWSFAVLL | WELVTR.EVP | FADLSNMEIG | MK.VALEGL. | R.TIPPGISP | 418 |

|       | XI         |            |            |            |     |
|-------|------------|------------|------------|------------|-----|
| Csk   | AVYEVMKN   | CWHLDAAMRP | SFLQLREQLE | HIKTHEL    |     |
| Yes   | SLHELMKL   | CWKKDPDERP | TFEYIQSFLE | ........   |     |
| Ctrl  | QVAAIIEG   | CWTNEPWKRP | SFATIMDLLR | PL.....    |     |
| B-raf | PKAMKRLMAECLKKKRDERP | LFPQILASIE | LLARSLP    |     |
| Ilk   | HVCKLMKI   | CMNEDPAKRP | KFDMIVPILE | KMQDK..    | 451 |

Fig. 1b

```
ANKYRIN       -G-TPLH-AA--GH---V--LL--GA--N----
CONSENSUS                   A                D

ANK1    33HGFSPLHWACREGRSAVVEMLIMRGARINVMNR
ANK2      GDDTPLHLAASHGHRDIVQKLLQYKADINAVNE
ANK3      HGNVPLHYACFWGQDQVAEDLVANGALVSICNK
ANK4      YGEMPVDKAKAPLRELLRERAEKMGQNLNRIPY164
```

Fig. 1c

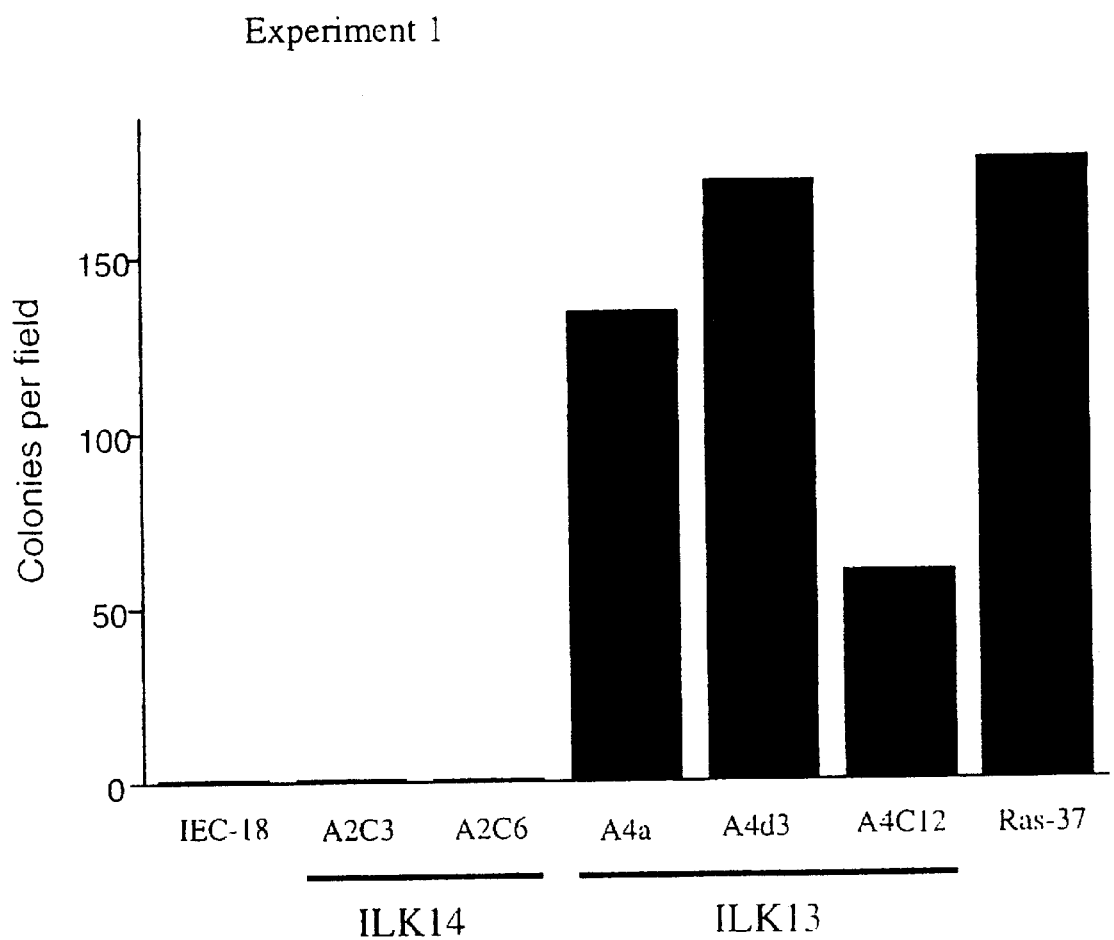
Fig. 4e (continued on page 21/23)

INTEGRIN-LINKED KINASE AND ITS USES

CROSS-REFERENCE TO RELATED APPLICATION

This application is a continuation in part of U.S. patent application Ser. No. 08/752,345, filed Nov. 19, 1996 abandoned, Dec. 4, 1997; which claims priority to Provisional Application No. 60/009,074, filed Dec. 21, 1995.

BACKGROUND

Proteins of the extracellular matrix (ECM) act to influence fundamental cell and tissue behaviors. ECM regulates cell structure, growth, survival, differentiation, motility and, at the organismal level, proper development. ECM proteins interact with cells via a class of cell membrane spanning receptors called integrins. ECM acts as a biological signal, where the integrin receptor is a specific transducer across the cell's plasma membrane of this signal. Integrins are also important in proliferative disorders, mediating such processes as wound healing and inflammation, angiogenesis, as well as tumor migration and invasion.

A major biochemical response to ECM integrin interactions is elevation of an enzymatic activity known as protein phosphorylation. Phosphorylation is important in signal transduction mediated by receptors for extracellular biological signals such as growth factors or hormones. For example, many cancer causing genes (oncogenes) are protein kinases, enzymes that catalyze protein phosphorylation reactions, or are specifically regulated by phosphorylation. In addition, a kinase can have its activity regulated by one or more distinct protein kinases, resulting in specific signaling cascades.

Research on signal transduction over the years has clearly established the importance of direct, protein-protein interactions in the cytoplasm as a major mechanism underlying the specification of signaling pathways. These interactions can, in part, be those between a receptor and a cytoplasmic protein kinase, or between a protein kinase and its substrate molecule(s).

A number of known protein kinases, such as mitogen-activated kinase (MAPK), focal adhesion kinase (FAK), and protein kinase C (PKC), have their kinase activity stimulated by integrin-ECM interaction. For example, see Maguire et al. (1995) J Exp Med 182:2079–2090; Richardson and Parsons (1995) Bioessays 17:229–236; Morino et al. (1995) J. Biol. Chem. 270:269–273; and Nojima et al. (1995) J Biol Chem 270:15398–15402. However, no cellular protein kinase has been identified to date that has been demonstrated to bind to an integrin molecule under physiological conditions. As such is the case, the direct molecular connection between integrins and the ECM-induced phosphorylation of cellular proteins is unclear. As such is the case, if the direct molecular connection between integrins and the ECM-induced phosphorylation of cellular proteins were determined, products which modulated that connection would be useful therapeutics. These products could be used to modulate cell growth, cell adhesion, cell migration and cell invasion. If it were determined that a specific kinase regulates integrin function, products that regulate (for example, inhibit) the activity of that kinase could be used for the treatment of cancer, leukemia, solid tumors, chronic inflammatory disease, arthritis and osteoporosis, among other indications.

Relevant Literature

A review of integrin mediated signal transduction in oncogenesis may be found in Dedhar (1995) Cancer Metastasis Rev 14:165–172. Hannigan et al. (1995) 86th (Annual Meeting of the American Institute for Cancer Research, provide a brief abstract directed to the cloning of a novel protein kinase associated with beta 11 integrin cytoplasmic tails. Hannigan et al. (1995) Molecular Biology of the Cell suppl. 6, p. 2244, is an abstract directed to the effect of overexpression of a novel integrin linked kinase (ILK) in induction of a transformed phenotype and cyclin D1 expression. Rosales et al. (1995) Biochim Biophys Acta 1242:77–98 reviews signal transduction by cell adhesion receptors. Signaling by cell adhesion receptors may, involve aspects that impinge on previously known signaling pathways including the RTK/Ras pathway and serpentine receptor/G protein pathways. A possible signaling role for the Syk tyrosine kinase is described in Lin et al. (1995) J Biol Chem 270:16189–16197.

Miyamoto et al. (1995) Science 267:883–885 compare the roles of receptor occupancy and aggregation on integrin receptor mediation of cell adhesion, signal transduction, and cytoskeletal organization. An EST sequence is provided by EMBL sequence DNA library accession no. p H70160, the Wash. U.—Merck EST project.

SUMMARY OF THE INVENTION

Isolated nucleotide compositions and sequences are provided for integrin linked kinase (ILK) genes. The ILK nucleic acid compositions find use in identifying homologous or related genes; for production of the encoded kinase; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like.

BRIEF DESCRIPTION OF THE DRAWINGS

FIGS. 1a–1e Yeast two-hybrid cloning, characterization, and expression of ILK. a, The full length ILK cDNA. b, Homology with protein kinase subdomains I to XI. c, Amino acid residues comprising ankyrin repeats. d, BIT-9 used to probe RNA from human tissues. e, Analysis of whole cell lysates of mouse, rat and human cell lines.

DESCRIPTION OF THE SPECIFIC EMBODIMENTS

Figure 1D:
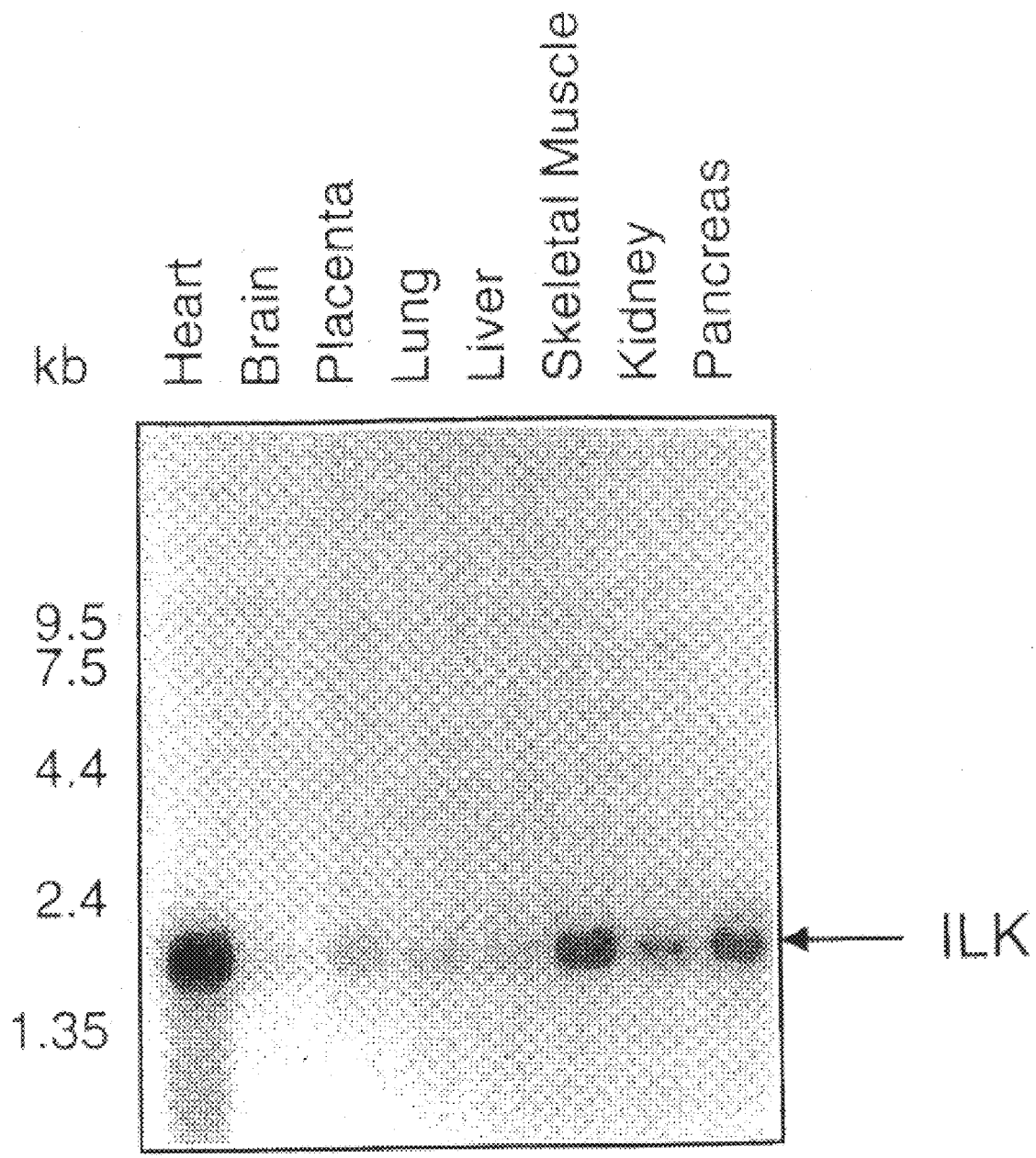

Nucleic acid compositions encoding integrin linked kinase (ILK) are provided. They are used in identifying homologous or related genes; in producing compositions that modulate the expression or function of its encoded protein; for gene therapy; mapping functional regions of the protein; and in studying associated physiological pathways. The ILK gene product (herein p59ILK) is a serine threonine kinase having two functional domains, identified by comparison of the ILK sequence against those found in current protein databases. These are the catalytic domain, responsible for phosphotransferase activity (kinase domain), and a non-overlapping domain in the amino terminus, comprised of four contiguous ankyrin-like repeats.

Modulation of ILK gene activity in vivo is used for prophylactic and therapeutic purposes, such as treatment of cancer, investigation of integrin signaling pathway function, identification of cell type based on expression, and the like. The protein is useful as an immunogen for producing specific antibodies, in screening for biologically active agents that act in the integrin signaling pathway and for therapeutic and prophylactic purposes.

The present invention demonstrates a physical linkage between integrin and ILK. Dysregulated expression of ILK protein modulates the function of integrins, thus providing a biological link between ILK and integrin. Dysregulated expression of ILK modulates cell growth, cell adhesion, cell migration and cell invasion. Hence, products that modulate the expression and/or activity of ILK have a therapeutic effect in the treatment of cancer, leukemia, solid tumors, chronic or acute inflammatory disease, arthritis and osteoporosis, among other indications.

Characterization of ILK

The human gene sequence of ILK is provided as SEQ ID NO:1, the encoded polypeptide product as SEQ ID NO:2. The ILK protein is encoded by a 1.8 kilobase pair messenger RNA (1.8 kb mRNA). The sequence of this mRNA was used to deduce the primary amino acid sequence of the protein, which has a predicted molecular weight of 50 kiloDaltons (kDa). The recombinant protein migrates on analytical polyacrylamide electrophoresis gels with an apparent molecular weight of 59 kDa, in rough agreement with the predicted size. p59ILK is a serine threonine kinase having two functional domains, identified by comparison of the ILK sequence against those found in current protein databases. These are the catalytic domain, responsible for phosphotransferase activity (kinase domain), and a non-overlapping domain in the amino terminus, comprised of four contiguous ankyrin-like repeats.

The function of ankyrin repeats in ILK is to mediate protein-protein interactions. The ILK ankyrin repeat domain is not required for the binding of $p59^{ILK}$ to integrin, and it is predicted to mediate the interaction of $p59^{ILK}$ with other cellular protein(s). Thus, $p59^{ILK}$ bridges integrin in the plasma membrane with intracellular proteins active regulating the cell's response to ECM signals. These proteins are likely to be located in the cytoplasm, or as part of the cell's structural framework (cytoskeleton).

ILK has novel structural and functional features. The molecular architecture is unusual, in that a protein kinase and an ankyrin repeat domain are contained within the same protein. The kinase domain has a high degree of similarity to other kinase sequences in existing databases, and can be divided into typical subdomains (I through XI) based on this conserved structure. However one amino acid in subdomain VIb of all other protein kinase domains is not present in ILK. Despite this unique structural feature, ILK clearly acts as a protein kinase, and thus represents a prototype member of a new subfamily of protein kinase molecules.

ILK regulates integrin extracellular activity (ECM interactions) from inside the cell via its direct interaction with the integrin subunit (colloquially known as inside-out signaling). Interfering with ILK activity allows the specific targeting of integrin function, while leaving other essential signaling pathways intact. Moreover, increasing the levels of cellular ILK activity short circuits the normal requirement for adhesion to ECM (i.e. integrin function) in regulating cell growth. Thus, inhibiting ILK activity inhibits anchorage-independent (i.e. cancerous) cell growth.

The ILK chromosomal locus is mapped to region 11p15. A subset of breast carcinomas displays LOH for markers in chromosomal region 11p15.5. This region has also been implicated in an inherited form of cardiac arrythmia, the long QT syndrome. A high level of expression of ILK mRNA indicates an integrin-independent function for ILK in cardiac tissue.

In untransformed intestinal epithelial cells, the kinase activity of ILK is inhibited upon cell-extracellular matrix interactions, and overexpression of constitutively active ILK results in anchorage-independent growth and tumorigenicity in nude mice. A consequence of elevation of ILK levels is a disruption of cell-cell interactions and manifestation of fibroblastic cell morphology and phenotypic properties, which include formation of a fibronectin matrix and invasion of collagen gels.

Overexpression of ILK results in a downregulation of E-cadherin expression, formation of a complex between β-catenin and the HMG transcription factor, LEF-1, translocation of β-catenin to the nucleus, and transcriptional activation by this LEF-1/β-catenin complex. LEF-1 protein expression is rapidly modulated by cell detachment from the extracellular matrix, and LEF-1 protein levels are constitutively upregulated upon ILK overexpression. These effects are specific for ILK.

Overexpression of ILK stimulates fibronectin matrix assembly in epithelial cells. The integrin-linked kinase activity is involved in transducing signals leading to the up-regulation of fibronectin matrix assembly, as overexpression of a kinase-inactive ILK mutant fails to enhance the matrix assembly. The increase in fibronectin matrix assembly is accompanied by a substantial reduction in cellular E-cadherin. The increased fibronectin matrix assembly is associated with an increased potential for tumor growth in vitro and in vivo.

Identification of ILK Sequences

Homologs of ILK are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). Nucleic acids that are substantially identical to the provided ILK sequences, e.g.

allelic variants, genetically altered versions of the gene, etc., bind to the provided ILK sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215:403–10. The sequences provided herein are essential for recognizing ILK related and homologous proteins in database searches.

ILK nucleic acid compositions

Nucleic acids encoding ILK may be cDNA or genomic DNA or a fragment thereof. The term ILK gene shall be intended to mean the open reading frame, encoding specific ILK polypeptides, introns, as well as adjacent 5 and 3 non-coding nucleotide sequences involved in the regulation of expression, up to about 20 kb beyond the coding region, but possibly further in either direction. The gene may be introduced into an appropriate vector for extrachromosomal maintenance or for integration into a host genome. The term cDNA as used herein is intended to include all nucleic acids that share the arrangement of sequence elements found in native mature mRNA species, where sequence elements are exons and 3 and 5 non-coding regions. Normally mRNA species have contiguous exons, with the intervening introns, when present, removed by nuclear RNA splicing, to create a continuous open reading frame encoding a ILK protein.

A genomic sequence of interest comprises the nucleic acid present between the initiation codon and the stop codon, as defined in the listed sequences, including all of the introns that are normally present in a native chromosome. It may further include the 3 and 5 untranslated regions found in the mature mRNA. It may further include specific transcriptional and translational regulatory sequences, such as promoters, enhancers, etc., including about 1 kb, but possibly more, of flanking genomic DNA at either the 5 or 3 end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where ILK is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) Mol Med 1: 194–205; Mortlock et al. (1996) Genome Res. 6: 327–33; and Joulin and Richard-Foy (1995) Eur J. Biochem 232: 620–626.

The regulatory sequences may be used to identify cis acting sequences required for transcriptional or translational regulation of ILK expression, especially in different tissues or stages of development, and to identify cis acting sequences and trans acting factors that regulate or mediate ILK expression. Such transcription or translational control regions may be operably linked to a ILK gene in order to promote expression of wild type or altered ILK or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. Regions of the provided sequence that are of interest as fragments include the 5' end of the gene, i.e. a portion of the sequence set forth in SEQ ID NO:1, nucleotides 1 to 1100.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The ILK genes are isolated and obtained in substantial purity, generally as other than an intact chromosome. Usually, the DNA will be obtained substantially free of other nucleic acid sequences that do not include a ILK sequence or fragment thereof generally being at least about 50%, usually at least about 90% pure and are typically recombinant, i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of ILK gene expression in the sample.

The sequence of a ILK gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993) Biotechniques 14:22; Barany (1985) Gene 37:111–23; Colicelli et al. (1985) Mol Gen Genet 199:537; and Prentki et al. (1984) Gene 29:303–13. Methods for site specific mutagenesis can be found in Sambrook et al., Molecular Cloning: A Laboratory Manual, CSH Press 1989, pp. 15.3–15.108; Weiner et al., Gene 126:35–41 (1993); Sayers et al. Biotechniques 13:592–6 (1992); Jones and Winistorfer, Biotechniques 12:528–30 (1992); Barton et al., Nucleic Acids Res 18:7349–55 (1990); Marotti and Tomich, Gene Anal Tech 6:67–70 (1989); and Zhu, Anal Biochem 177:120–4 (1989). Such mutated genes may be used to study structure-function relationships of ILK, or to alter properties of the protein that affect its function or regulation.

ILK Polypeptides

The subject gene may be employed for producing all or portions of ILK polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to an ILK gene, or may be derived from exogenous sources.

The peptide may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the ILK gene in eukaryotic cells, where the ILK protein will benefit from native folding and post-translational modifications. Small peptides can also be synthesized in the laboratory. Peptides that are subsets of the complete ILK sequence may be used to identify and investigate parts of the protein important for function, such as the GTPase binding domain, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed ILK polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of ILK. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

Diagnostic Uses

DNA-based reagents derived from the sequence of ILK, e.g. PCR primers, oligonucleotide or cDNA probes, as well as antibodies against p59ILK, are used to screen patient samples, e.g. biopsy-derived tumors, inflammatory samples such as arthritic synovium, etc., for amplified ILK DNA, or increased expression of ILK mRNA or protein. DNA-based reagents are designed for evaluation of chromosomal loci implicated in certain diseases e.g. for use in loss-of-heterozygosity (LOH) studies, or design of primers based on ILK coding sequence.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in an ILK coding region or control regions is associated with disease, particularly cancers and other growth abnormalities. Disease associated polymorphisms may include deletion or truncation of the gene, mutations that alter expression level, that affect the binding activity of the protein to integrin, kinase activity domain, etc.

Changes in the promoter or enhancer sequence that may affect expression levels of ILK can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express ILK may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of techniques may be found in Sambrook, et al. Molecular Cloning: A Laboratory Manual, CSH Press 1989, pp.14.2–14.33. Alternatively, various methods are known in the art that utilize oligonucleotide ligation as a means of detecting polymorphisms, for examples see Riley et al. (1990) N.A.R. 18:2887–2890; and Delahunty et al. (1996) Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4, 7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^3H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type ILK sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in ILK may be based on the functional or antigenic characteristics of the protein. Protein truncation assays are useful in detecting deletions that may affect the biological activity of the protein. Various immunoassays designed to detect polymorphisms in ILK proteins may be used in screening. Where many diverse genetic mutations lead to a particular disease phenotype, functional protein assays have proven to be effective screening tools. The activity of the encoded ILK protein in kinase assays, binding of integrins, etc., may be determined by comparison with the wild-type protein.

Antibodies specific for a ILK may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal ILK in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) Genomics 24:225–233; Ziegle et al. (1992) Genomics 14:1026–1031; Dib et al., supra.

Modulation of Gene Expression

From a therapeutic point of view, inhibiting ILK activity has a therapeutic effect on a number of proliferative disorders, including inflammation and cancer. Inhibition is achieved in a number of ways. Antisense ILK sequences may be administered to inhibit expression. Pseudo-substrate inhibitors, for example, a peptide that mimics a substrate for ILK may be used to inhibit activity. Other inhibitors are identified by screening for biological activity in an ILK-based functional assay, e.g. in vitro or in vivo ILK kinase activity.

The ILK genes, gene fragments, or the encoded protein or protein fragments are useful in gene therapy to treat disorders associated with ILK defects. Expression vectors may be used to introduce the ILK gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or ILK protein may be introduced into tissues or host cells by any number of routes, including viral infection, microinjection, or fusion of vesicles. Jet injection may also be used for intramuscular administration, as described by Furth et al. (1992) Anal Biochem 205:365–368. The DNA may be coated onto gold microparticles, and delivered intradermally by a particle bombardment device, or "gene gun" as described in the literature (see, for example, Tang et al. (1992) Nature 356:152–154), where gold microprojectiles are coated with the ILK or DNA, then bombarded into skin cells.

Antisense molecules can be used to down-regulate expression of ILK in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S'-5-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5'-methyl-2'-deoxycytidine and 5'-bromo-2'-deoxycytidine for deoxycytidine. 5'-propynyl-2'-deoxyuridine and 5'-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) Nucl. Acids Res 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) Appl Biochem Biotechnol 54:43–56.

Genetically Altered Cell or Animal Models for ILK Function

The subject nucleic acids can be used to generate transgenic animals or site specific gene modifications in cell lines. Transgenic animals may be made through homologous recombination, where the normal ILK locus is altered. Alternatively, a nucleic acid construct is randomly integrated into the genome. Vectors for stable integration include plasmids, retroviruses and other animal viruses, YACs, and the like.

The modified cells or animals are useful in the study of ILK function and regulation. For example, a series of small deletions and/or substitutions may be made in the ILK gene to determine the role of different exons in integrin binding, kinase activity, oncogenesis, signal transduction, etc. Of interest are the use of ILK to construct transgenic animal models for cancer, where expression of ILK is specifically reduced or absent. Specific constructs of interest include anti-sense ILK, which will block ILK expression and expression of dominant negative ILK mutations. A detectable marker, such as lac Z may be introduced into the ILK locus, where upregulation of ILK expression will result in an easily detected change in phenotype.

One may also provide for expression of the ILK gene or variants thereof in cells or tissues where it is not normally expressed or at abnormal times of development. By providing expression of ILK protein in cells in which it is not normally produced, one can induce changes in cell behavior, e.g. through ILK mediated LEK-1 activity.

DNA constructs for homologous recombination will comprise at least a portion of the ILK gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., e.g. to determine the effect of a candidate drug on oncogenesis, downregulation of E-cadherin, upregulation of LEF-1, etc.

In Vitro Models for ILK Function

The availability of a number of components in the integrin signaling pathway allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other; utilization of GTP, etc. The components may be modified by sequence deletion, substitution, etc. to determine the functional role of specific domains.

Drug screening may be performed using an in vitro model, a genetically altered cell or animal, or purified ILK protein. One can identify ligands or substrates that bind to, modulate or mimic the action of ILK. Areas of investigation include the development of cancer treatments, metastasis, etc.

Drug screening identifies agents that modulate ILK function. Agents that mimic its function are predicted to activate the process of cell division and growth. Conversely, agents that reverse ILK function may inhibit transformation. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of ILK, derived from crystallization of purified recombinant ILK protein, leads to the rational design of small drugs that specifically inhibit ILK activity. These drugs may be directed at specific domains of ILK, e.g. the kinase, ankyrin repeat domains, etc.

The term "agent" as used herein describes any molecule, e.g. protein or pharmaceutical, with the capability of altering or mimicking the physiological function of ILK. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic ILK function, such integrin binding, kinase activity, downregulation of E-cadherin, upregulation of LEF-1, binding properties, etc. For example, an expression construct comprising a ILK gene may be introduced into a cell line under conditions that allow expression. The level of ILK activity is determined by a functional assay, as previously described. In one screening assay, candidate agents are added, and the formation of fibronectin matrix is detected. In another assay, the ability of candidate agents to enhance ILK function is determined. A functional assay of interest detects the stimulation of cyclin D1 and/or cyclin A expression. Alternatively, candidate agents are added to a cell that lacks functional ILK, and screened for the ability to reproduce ILK in a functional assay.

The compounds having the desired pharmacological activity may be administered in a physiologically acceptable carrier to a host for treatment of cancer, etc. The compounds may also be used to enhance ILK function in wound healing, cell growth, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–10 wt %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Isolation of ILK cDNA

Figure 1E:
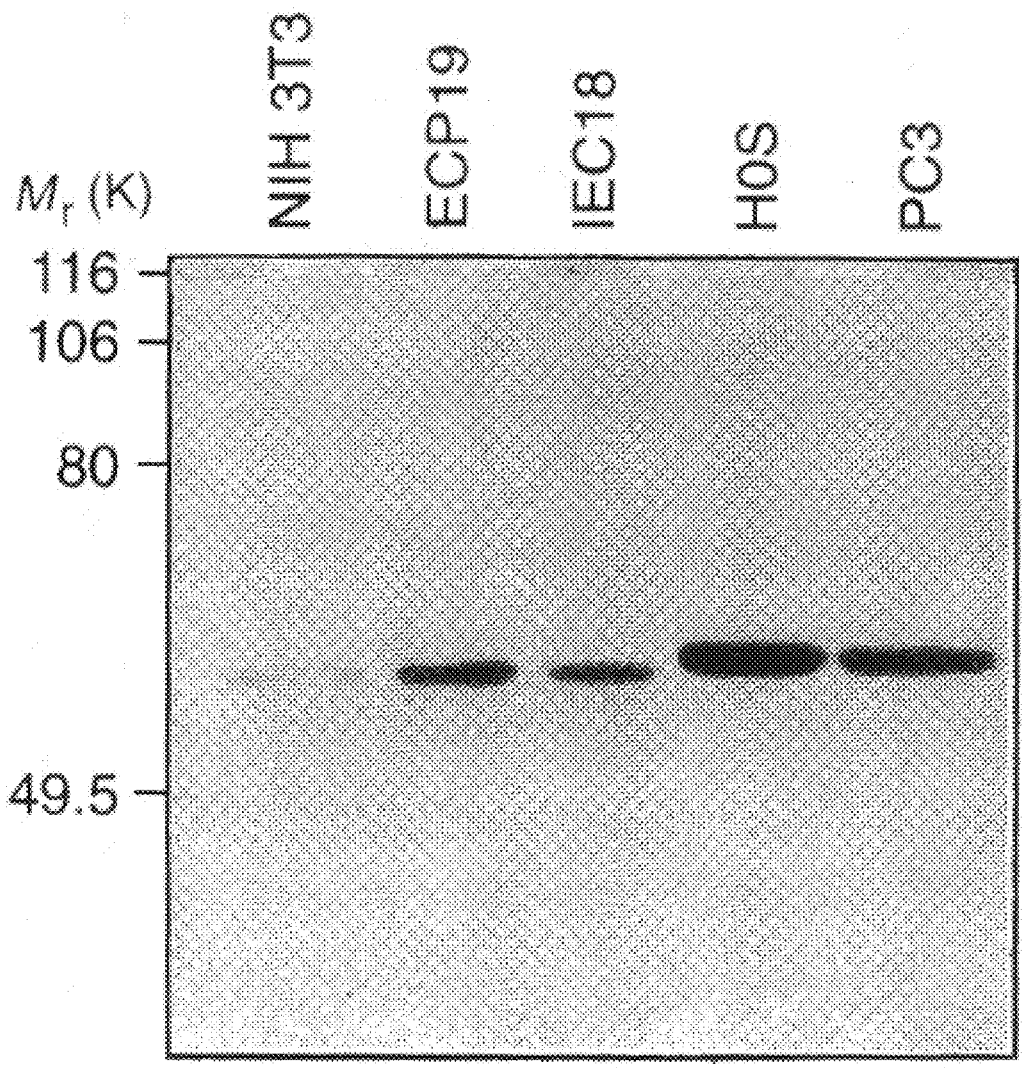

A partial CDNA, BIT-9, was isolated in a two-hybrid screen using a bait plasmid expressing the cytoplasmic domain of the $\beta_1$ integrin subunit. The BIT-9 insert was used to isolate clones from a human placental CDNA library. A 1.8 kb clone, Plac5, was found to contain a high degree of similarity to cDNAs encoding protein kinases (FIGS. 1a–c), and recognized a widely expressed transcript of 1.8 kb in Northern blots (FIG. 1d). Deduced amino acid residues 186–451 from Plac5 comprise a domain which is highly homologous with the catalytic domains of a large number of protein tyrosine and serine/threonine kinases (FIG. 1b). Residues 33–164 comprise four repeats of a motif originally identified in erythrocyte ankyrin (FIG. 1c), likely defining a domain involved in mediating additional protein-protein interactions. Affinity-purified anti-ILK antibodies (see methods described in Example 3) were used in Western blot analyses of mammalian cell extracts, and detected a conserved protein of apparent Mr of 59 kDa (p59ILK, FIG. 1e).

FIG. 1 shows yeast two-hybrid cloning, characterization, and expression of ILK. (a) The full length ILK cDNA, Plac5, was isolated from a human placental library using the BIT-9 insert. Plac5 contains a 1509 bp open reading frame, with a presumptive initiator Met at nt 157, and an AAUAAA signal 11 bp upstream of the polyadenylation site. In vitro transcription and translation of Plac5 in rabbit reticulocyte lysates yielded a protein of apparent Mr of 59 kDa (not shown). (b) A search of the PIR protein database indicated homology with protein kinase subdomains I to XI, as identified by Hanks et al. We note sequence variations in the ILK subdomains I, VIb, and VII, relative to catalytic domains of known protein kinases. Subdomain I (residues 199–213), does not have the typical GXGXXG motif, although this region in ILK is Gly-rich. In subdomain VIb, Asp328 of ILK may compensate for the lack of the otherwise conserved Asp319. In subdomain VII, the DFG triplet is absent in ILK. The integrin binding site maps to amino acid residues 293–451 (BIT-9). The ILK kinase domain is most highly related to the CTR1 kinase of *Arabidopsis thaliana* (30% identity, P<10). The CTR1, B-raf, Yes and Csk kinase domains are aligned with Plac5. (c) Amino acid residues 33–164 comprise four contiguous ankyrin repeats, as defined by Lux et. al. (d) BIT-9 was used to probe a blot of poly A+ selected RNA (MTN I, Clontech) from various human tissues. (e) Whole cell lysates of mouse, rat and human cell lines (10 μg/lane) were analyzed by Western blotting with the affinity-purified 92-2 antibody (see description of methods in Example 3). The ILK sequence data are available from GenBank under accession number U40282.

In order to construct integrin 'bait' plasmids, sequences encoding amino acid residues 738–798 of the $\beta_1$, and residues 1022–1049 of the $\alpha_5$ integrin subunits were amplified from full-length cDNAs. The primers used were (a) 5' amplification 5'-GGCCGMTTCGCTGGMTTGTTCTTATTGGC-3' and (b) 3' amplification 5'-GGCCGGATCCTCATTTTCCCTCATACTTCGG-3'. PCR products were directionally cloned into pEG202, creating the LexA fusion bait plasmids, pEG202$\beta_1$INT and pEG202$\alpha_5$INT. pEG202$\beta_1$INT and pEG202$\alpha_5$INT repressed β-gal expression from the pJK101 reporter by 50–60% and 70–75%, respectively, in host strain EGY48 (MATα, his3, trp1, ura3-52, LEU2::pLEU2-LexAop6, constructed by Erica Golemis, Massachussetts General Hospital), confirming nuclear expression of the LexA fusions. Co-transformation of baits with the pSH18-34 reporter verified they were transcriptionally inert. A galactose-inducible HeLa cDNA interactor library was present on the TRP+ vector, pJG4-5 (constructed by Jeno Gyuris, MGH). For the $\beta_1$ interaction trap, EGY48 was transformed sequentially with pEG202β$_1$INT, pSH18-34 and pJG4-5, using the lithium acetate protocol (transformation efficiency=5–6×10$^4$/μg). 2×10$^6$ primary transformants were screened, of which forty-nine interacting clones were confirmed. The most frequent isolate (31/49) was a 700 bp insert, BIT-9. Retransformation of EGY48 with the BIT-9, pSH18-34, and pEG202β$_1$INT plasmids resulted in strong β-galactosidase expression, confirming the interaction. An identical screen, using pEG202α$_5$INT as bait, resulted in the isolation of 16 positives, none of which were represented in the set of 49 β$_1$ interactors. Trapped inserts were used to screen WM35 human melanoma λgt10, and human placental λgt11 cDNA libraries, using standard procedures. cDNA sequencing of multiple clones from each library was done using the dideoxy chain termination method (Sequenase 2.0, U.S. Biochemical). For data analysis we used the Genetics Computer Group software package (version 7.0), and database searches were accomplished via the BLAST server at the National Center for Biotechnology Information.

EXAMPLE 2

Analysis of ILK in vitro

Figure 2A:
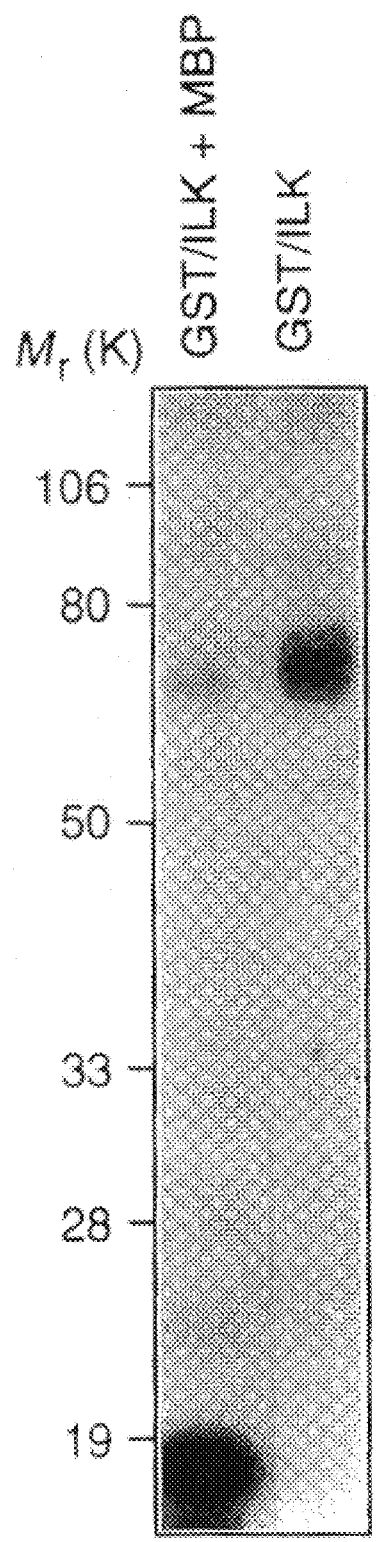
FIGS. 2a–2c In vitro and immune-complex kinase assays. a, In vitro kinase reactions., b, Immune complexes. c, $^{32}$P-labeled products isolated and analyzed for phosphoamino acid content.
Figure 2B:
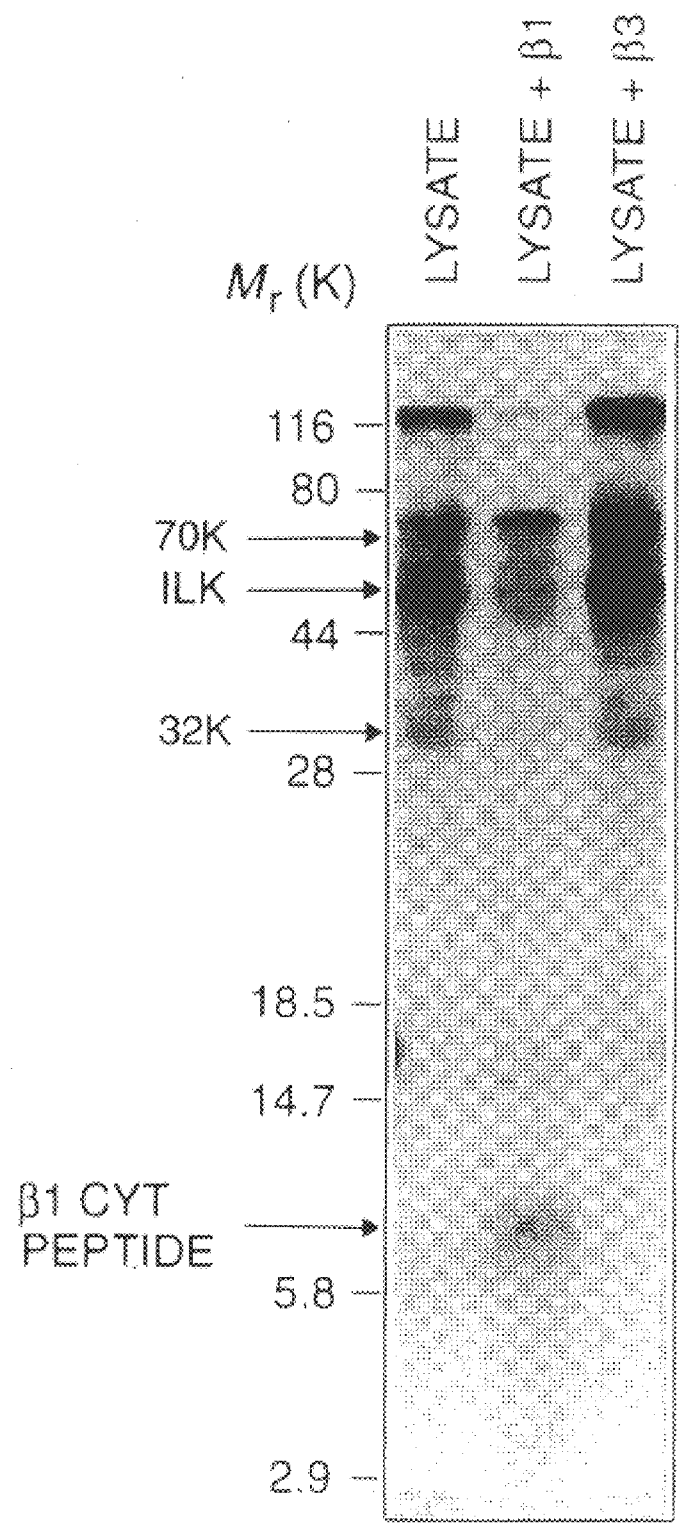

For analysis of kinase activity in vitro, a bacterially-expressed fusion protein, GST-ILK$^{132}$, was SDS-PAGE band purified, and incubated with [γ-$^{32}$P]ATP in the presence or absence of the exogenous substrate myelin basic protein (FIG. 2). GST-ILK$^{132}$ autophosphorylated and labeled MBP efficiently in these assays (FIG. 2a). Anti-GST-ILK$^{132}$ (antibody 91-3) immunoprecipitates of PC3 cell lysates were incubated with [γ-$^{32}$P]ATP, similar to experiments performed with purified recombinant GST-ILK$^{132}$. ILK immune complexes labeled a protein of apparent Mr of 59 kDa (FIG. 2b), corresponding to p59$^{ILK}$, as well as cellular proteins of apparent Mr 32 kDa and 70 kDa, which may be endogenous ILK substrates (FIG. 2b). Cellular phosphoproteins (serine/threonine) of approximately 32 kDa and 70 kDa, were also seen in β$_1$ integrin-specific immune complex kinase assays.

Figure 2C:
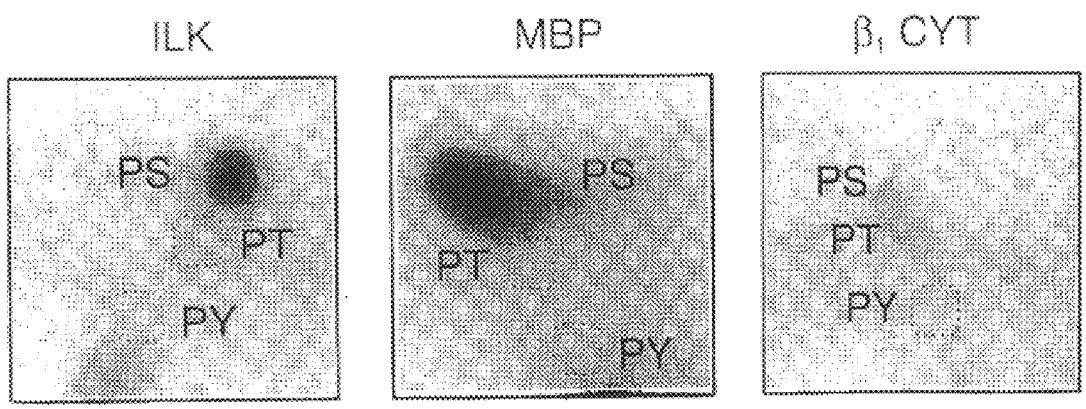

In ILK immune complex kinase assays a synthetic peptide representing the β$_3$ cytoplasmic domain was phosphorylated, while a similar peptide representing the β$_3$ cytoplasmic domain was not detectably labeled by p59$^{ILK}$. The β$_1$ peptide selectively inhibited autophosphorylation of ILK in these reactions (FIG. 2b), further indicating a differential interaction of the peptides with ILK. The results demonstrating phosphorylation of synthetic β peptides by endogenous ILK are identical to those seen with recombinant GST-ILK$^{132}$, and indicate the potential substrate preference of ILK for the β$_1$ cytoplasmic tail. This does not, however, necessarily rule out an interaction between ILK and the β$_3$ integrin cytoplasmic domain. Phosphoamino acid analyses of labeled p59$^{ILK}$ and MBP from the immune complex kinase assays detected only phosphoserine in both substrates (FIG. 2c), as was the case for phosphorylation of these substrates by GST-ILK$^{132}$. The β$_1$ peptide was labeled on serine and threonine residues, with approximately equal stoichiometry (FIG. 2). As a control, anti-FAK immune complexes from the same lysates were analyzed for phosphorylation of MBP, and phosphotyrosine was readily detected.

FIG. 2 shows in vitro and immune-complex kinase assays. a, In vitro kinase reactions containing 2 μg of gel-purified GST-ILK132, with and without 5 μg of myelin basic protein (MBP, Upstate Biotechnologies, Inc.), were analyzed by 10% SDS-PAGE. b, Immune complexes were generated from PC3 whole cell lysates, using affinity-purified 91-3 antibody. Complexes were assayed for kinase activity, with and without addition of 5 μg/reaction of synthetic peptides, representing β$_1$ or β$_3$ integrin cytoplasmic domains or MBP. Products were analyzed by 15% SDS-PAGE (kDa markers at left), and migration of peptides confirmed by Coomassie Blue staining. c, $^{32}$P-labeled products from the anti-ILK immune complex kinase reactions shown in b, were isolated and analyzed for phosphoamino acid content. Anti-FAK immune complex kinase assays demonstrated phosphotyrosine on MBP.

Protein kinase assays were performed in 50 μl kinase reaction buffer (50 mM HEPES pH 7.0, 10 mM MnCl$_2$, 10 mM MgCl$_2$, 2 mM NaF, 1 mM Na$_3$VO$_4$), containing 10 μCi [γ-$^{32}$P]ATP. Reactions were incubated at 30° C. for 20 min, and stopped by the addition of SDS-PAGE sample buffer. For assay of recombinant ILK activity, GST-ILK$^{132}$ was adsorbed from bacterial lysates onto glutathione-agarose beads, or GST-ILK$^{132}$ was band-purified from 10% SDS-PAGE gels. For immune complex kinase assays, affinity-purified 91-3 anti-ILK antibody (FIG. 3) was used to generate immunoprecipitates from NP-40 lysates (150 mM NaCl, 1% (v/v) NP-40, 0.5% (w/v) sodium deoxycholate, 50 mM HEPES pH 7.5, 1 μg/ml each leupeptin and aprotinin, 50 μg/ml phenyl-methylsulfonyl flouride) of PC3 cells. Kinase reaction products were resolved on 10–15% SDS-PAGE gels, transferred to PVDF, and phosphoamino acid analysis performed according to a published protocol.

EXAMPLE 3

Association of ILK and β integrin In Mammalian Cells

Figure 3A:
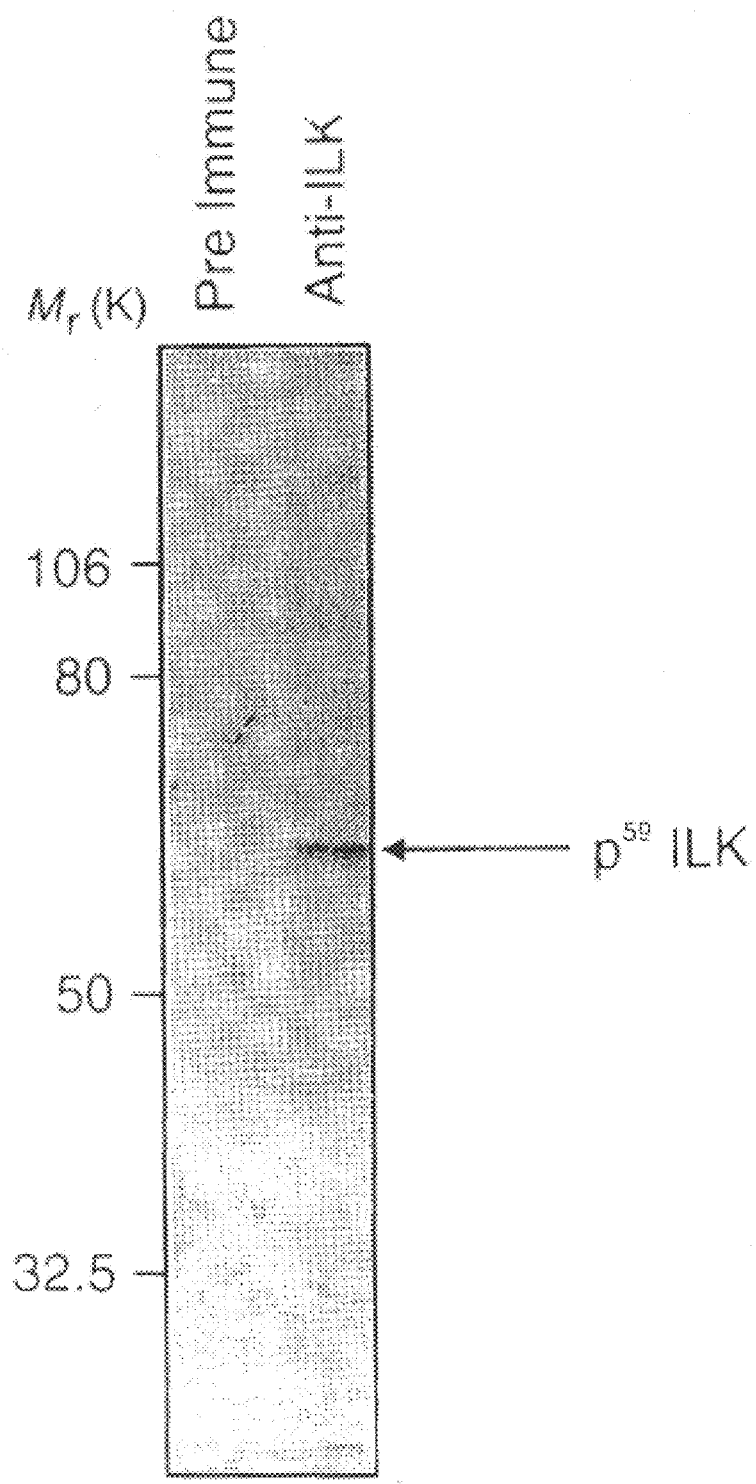
FIGS. 3a–3d Antibodies to GST-ILK$^{132}$ recognize p59$^{ILK}$ in integrin co-immunoprecipitations. a, Unfractionated polyclonal anti-ILK sera specifically recognize a $^{35}$S-methionine, metabolically-labeled cellular protein. b, Affinity-purified antibody was adsorbed with GST-ILK agarose-GST. c, Polyclonal anti-integrin antibodies used to precipitate surface-biotinylated integrins from PC3 cells. d, Anti-1 monoclonal antibodies were used in co-precipitation analyses of lysates of PC3.
Figure 3B:
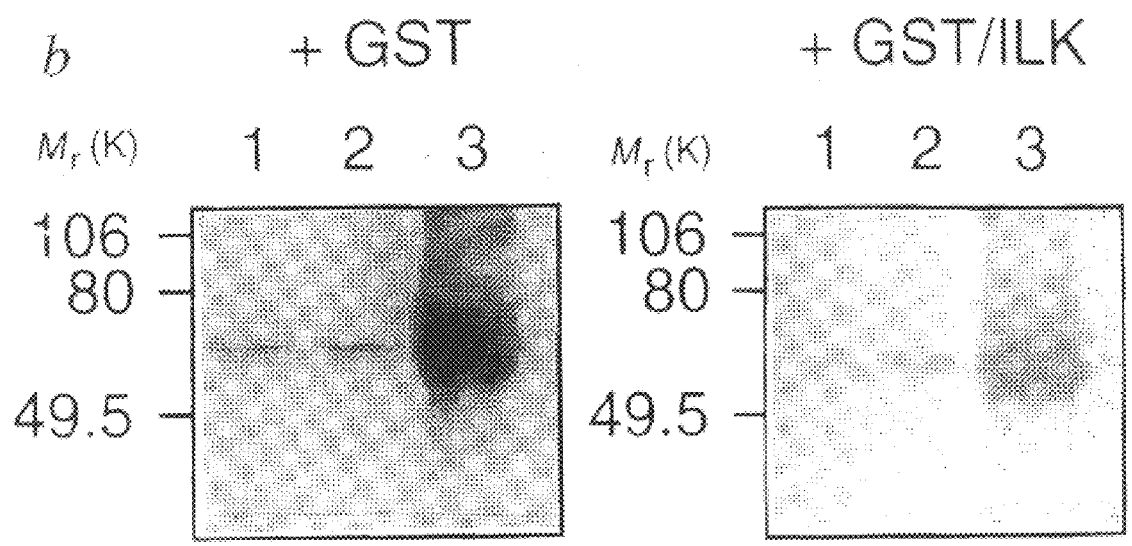
Figure 3C:
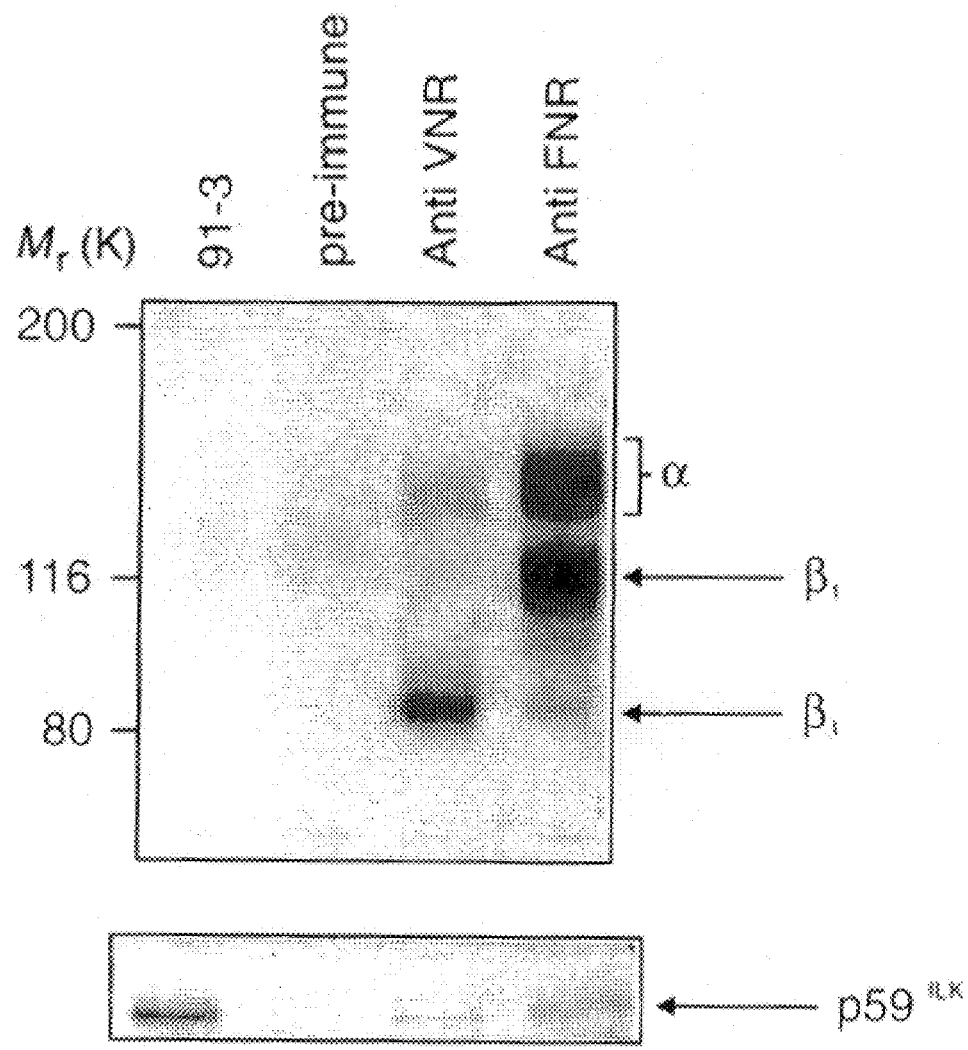
Figure 3D:
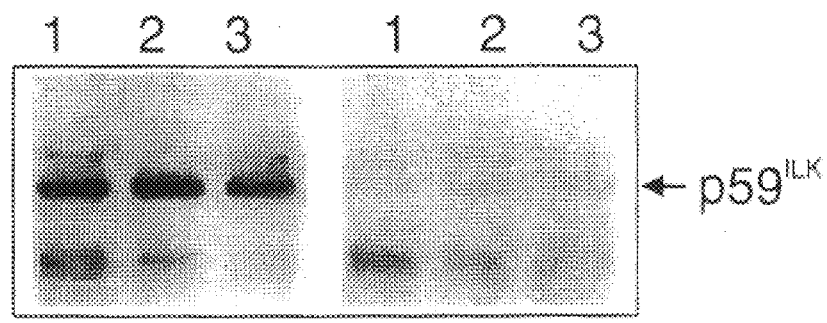

Immunofluorescence experiments indicated that ILK and β integrin co-localize in focal plaques. In order to test further for this association in intact mammalian cells, we performed co-immunoprecipitation assays in lysates of PC3 cells, in which integrin expression has been well-characterized. PC3 cell lysates were immunoprecipitated with specific anti-integrin antibodies, and immune complexes analyzed by Western blotting with the anti-ILK antibody, 92-2. The specificities of the anti-ILK antibodies were tested by immunoprecipitation and Western blotting (FIGS. 3a, b). We detected p59$^{ILK}$ in immune complexes obtained with anti-fibronectin receptor (FNR, α$_5$/α$_3$β integrin), and anti-vitronectin receptor (VNR, α$_v$β$_3$/β$_5$ integrin) antibodies, but not in those obtained with non-immune serum (FIG. 3c). Three anti-β$_1$ monoclonal antibodies also co-precipitated p59$^{ILK}$ from PC3 lysates, confirming the β integrin specificity of p59$^{ILK}$ interaction (FIG. 3d). The detection of p59$^{ILK}$ in anti-VNR immune complexes suggests that ILK may also interact with the β$_3$ and/or β$_5$ integrin subunit(s).

FIG. 3 shows that antibodies to GST-ILK$^{132}$ recognize p59$^{ILK}$ in integrin co-immunoprecipitations. a, Unfractionated polyclonal anti-ILK sera 91-3 (shown) and 92-2 specifically recognize a $^{35}$S-methionine, metabolically-labeled cellular protein, of apparent Mr of 59 kDa. A fluorograph is shown (En$^3$Hance, NEN). b, Affinity-purified 92-2 antibody was adsorbed with 165 μg of agarose-coupled GST-ILK$^{132}$, or agarose-GST, which preparations were used in parallel Western blots containing 10 μg/lane of whole cell lysates of PC3 cells, Jurkat T-lymphoblasts, or the 60 kDa GST-ILK$^{132}$. c, Polyclonal anti-integrin antibodies, specific for the fibronectin and vitronectin receptors, were used to precipitate surface-biotinylated integrins from PC3 cells, and immune complexes were then analyzed for the presence of p59$^{ILK}$, by Western blotting with affinity-purified, biotin-labeled 92-2 antibody. This result is representative of six independent experiments. d, Anti-$\beta_1$ monoclonal antibodies were used in co-precipitation analyses of NP-40 lysates of PC3: lane 1, $A_{II}B_2$; lane 2, anti-CD29; lane 3, 3S3. Western blotting of anti-$\beta_1$ immune complexes with affinity-purified, biotinylated 92-2 antibody (left). This blot was stripped and reprobed with the same concentration of biotinylated 92-2, adsorbed against an excess of GST-ILK$^{132}$ beads (right). We observe co-precipitation of p59$^{ILK}$ using a panel of 11 anti-$\beta_1$ monoclonals, but not with an anti-CD44 monoclonal antibody. The migration of p59$^{ILK}$ was confirmed in parallel lanes containing PC3 whole cell NP40 lysates. Markers at left, in kDa.

Amino acid residues 132–451 of ILK were expressed as a GST fusion protein, in E. coli. Recombinant GST-ILK$^{132}$ protein was purified and used to inject two rabbits. The resulting antisera, 91-3 and 92-2 (raised by Research Genetics, Inc.), were affinity-purified over a column of CNBr-Sepharose coupled GST-ILK$^{132}$. PC3 cells were metabolically labeled with 100 $\mu$Ci/ml [$^{35}$S]methionine/ [$^{35}$S]cysteine ([$^{35}$S] ProMix, 1000 Ci/mmol, Amersham), for 18 hours in cysteine/methionine-free MEM. For co-immunoprecipitation experiments PC3 cells were surface-labeled with sulfo-NHS-biotin (Pierce Chemicals), prior to lysis in NP-40 buffer. Polyclonal anti-fibronectin receptor (anti-FNR, Telios A108), and anti-vitronectin receptor (anti-VNR, Telios A109) antibodies were purchased from Gibco/BRL. 1–2 mg of NP-40 lysate was incubated at 4° C., with 2–3 $\mu$l/ml anti-FNR or anti-VNR antiserum, or 2 $\mu$g/ml of the anti-$\beta_1$ monoclonal antibodies $A_{II}B_2$ (C. Damsky, UC, San Francisco), anti-CD29 (Upstate Biotechnology, Inc.), and 3S3 (J. Wilkins, U Manitoba). Lysates were pre-cleared and immune complexes collected with Protein A-Sepharose. For Western blotting, RIPA lysates or immune complexes were subjected to 7.5% or 10% SDS-PAGE, and proteins then electrophoretically transferred to polyvinylidene fluoride membranes (Immobilon-P, Millipore). Membranes were blocked in 5% non-fat milk/Tris-buffered saline Tween-20, and incubated with 0.5 $\mu$g/ml affinity purified antibodies. Horseradish peroxidase-coupled goat anti-rabbit IgG was used in secondary incubations, followed by detection of reactive bands by enhanced chemiluminescence (ECL, Amersham). For blotting without use of secondary antibody (FIG. 3), affinity-purified 92-2 antibody was labeled with Biotin Hydrazide (Immunopure, Pierce Chemicals), according to the manufacturer's protocol, with visualization by peroxidase-conjugated streptavidin (Jackson ImmunoResearch Laboratories) and ECL. For re-probing, membranes were stripped according to manufacturer's instructions.

EXAMPLE 4

Overexpression of ILK Provides Growth Advantage

Figure 4A:
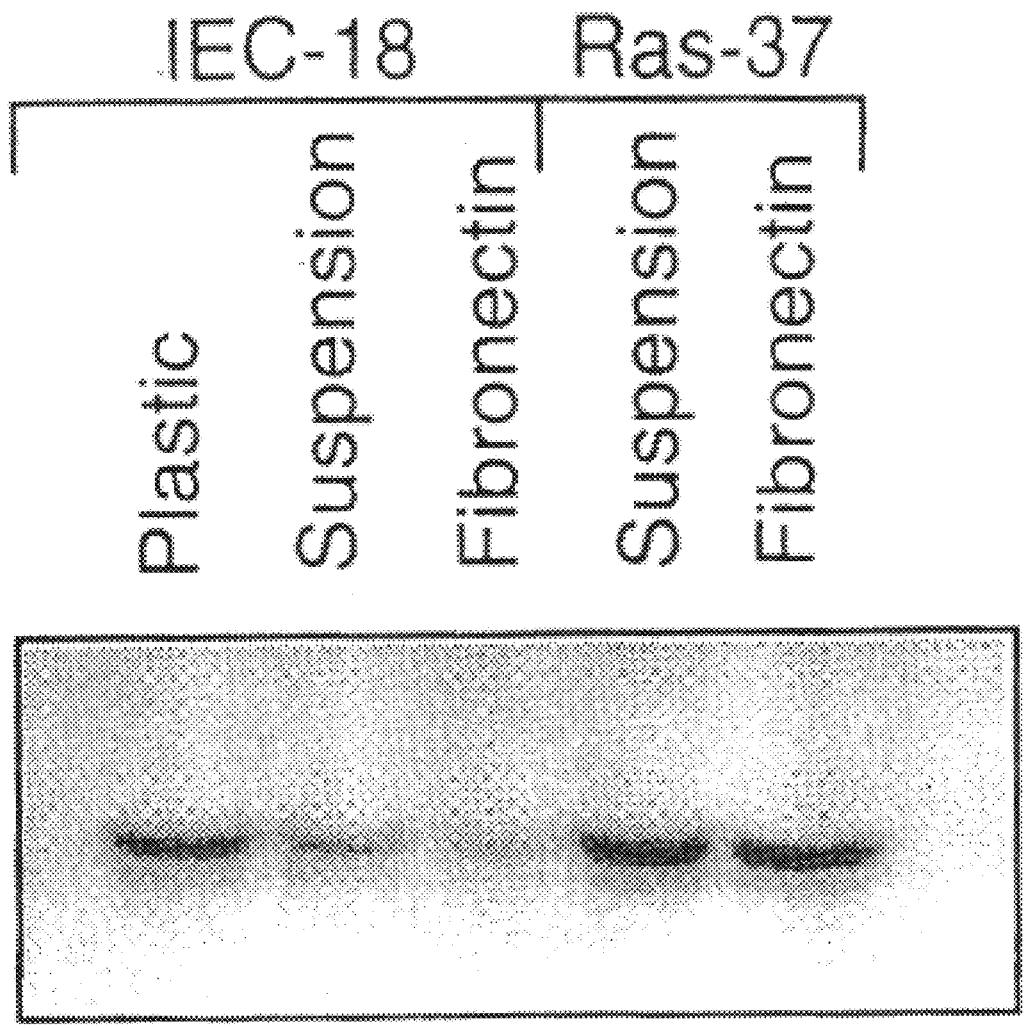
FIGS. 4a–4e Modulation of ILK kinase activity by ECM components. a, ILK phosphorylation of MBP was assayed. b, Expression levels of p59ILK. c, Representative p59$^{ILK}$ overexpressing clone ILK13-A4a on the ECM substrates. d, Adhesion of the ILK overexpressing clones to LN, FN and VN was quantified. e, ILK13, p59$^{ILK}$ overexpressing clones were assayed for colony growth.
Figure 4B:
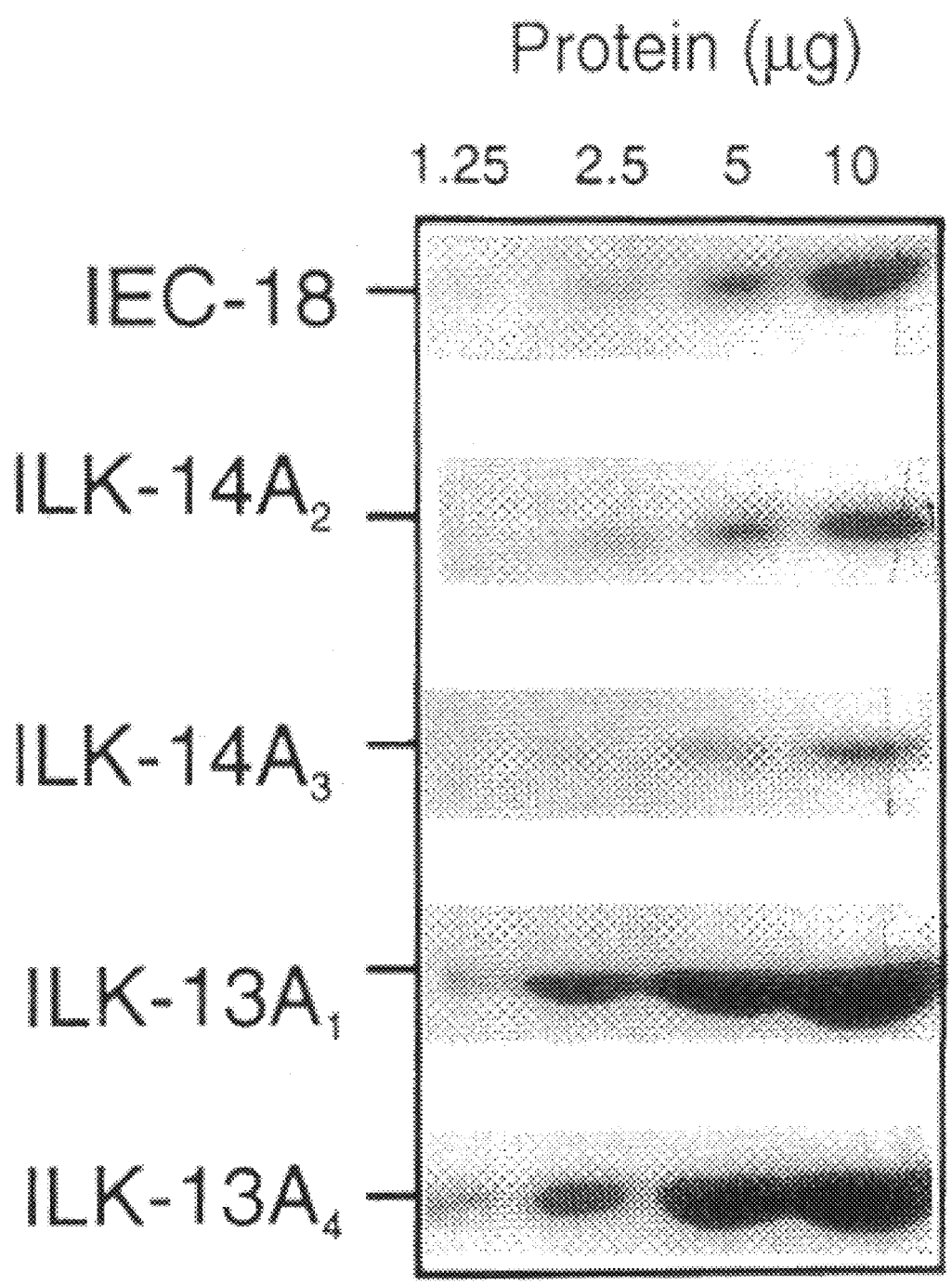
Figure 4C:
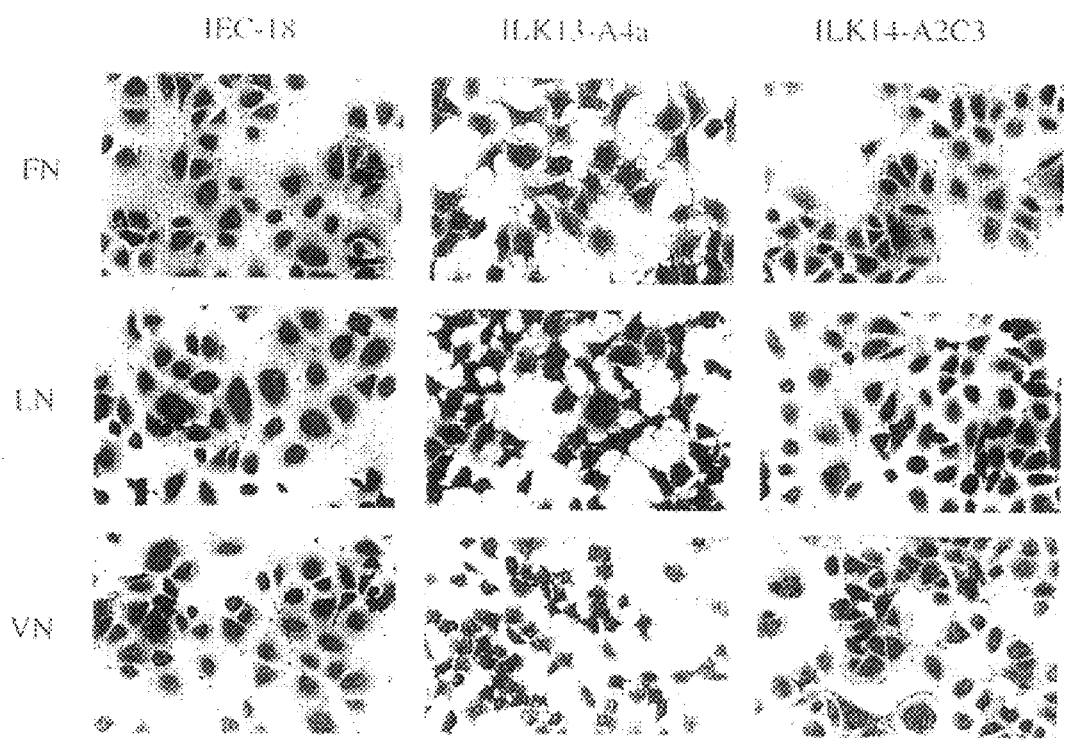
Figure 4D:
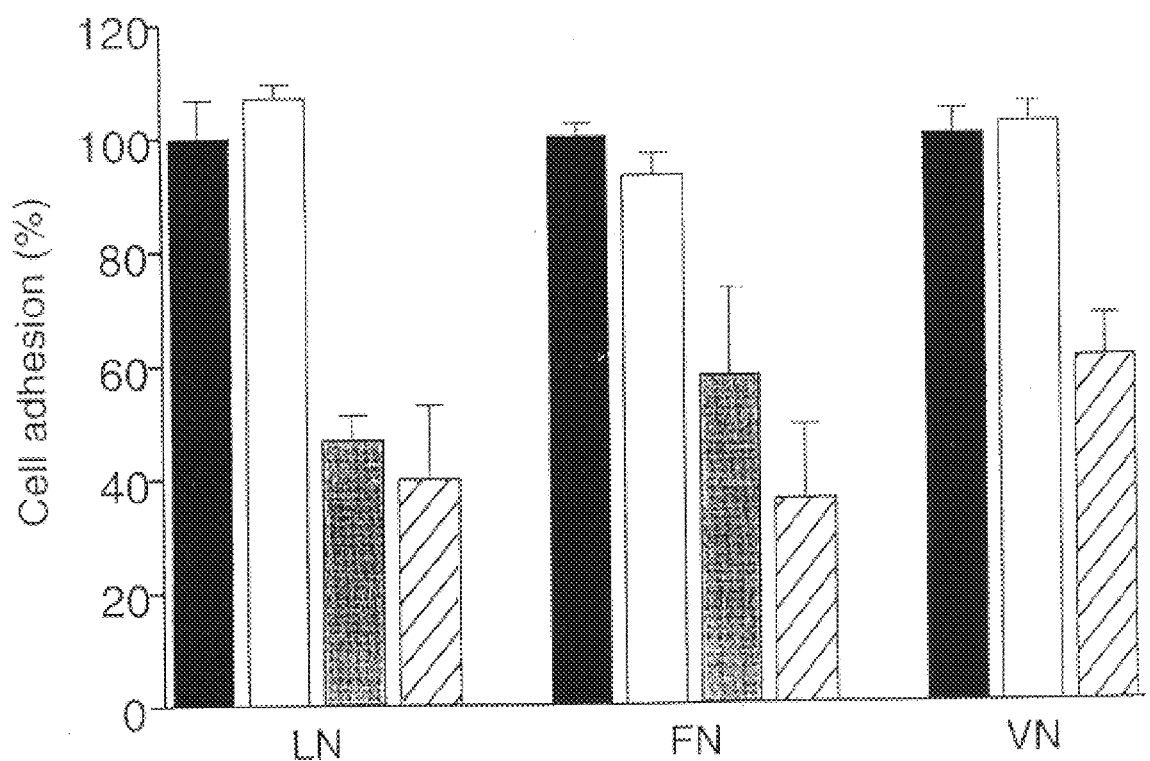
Figure 4E:
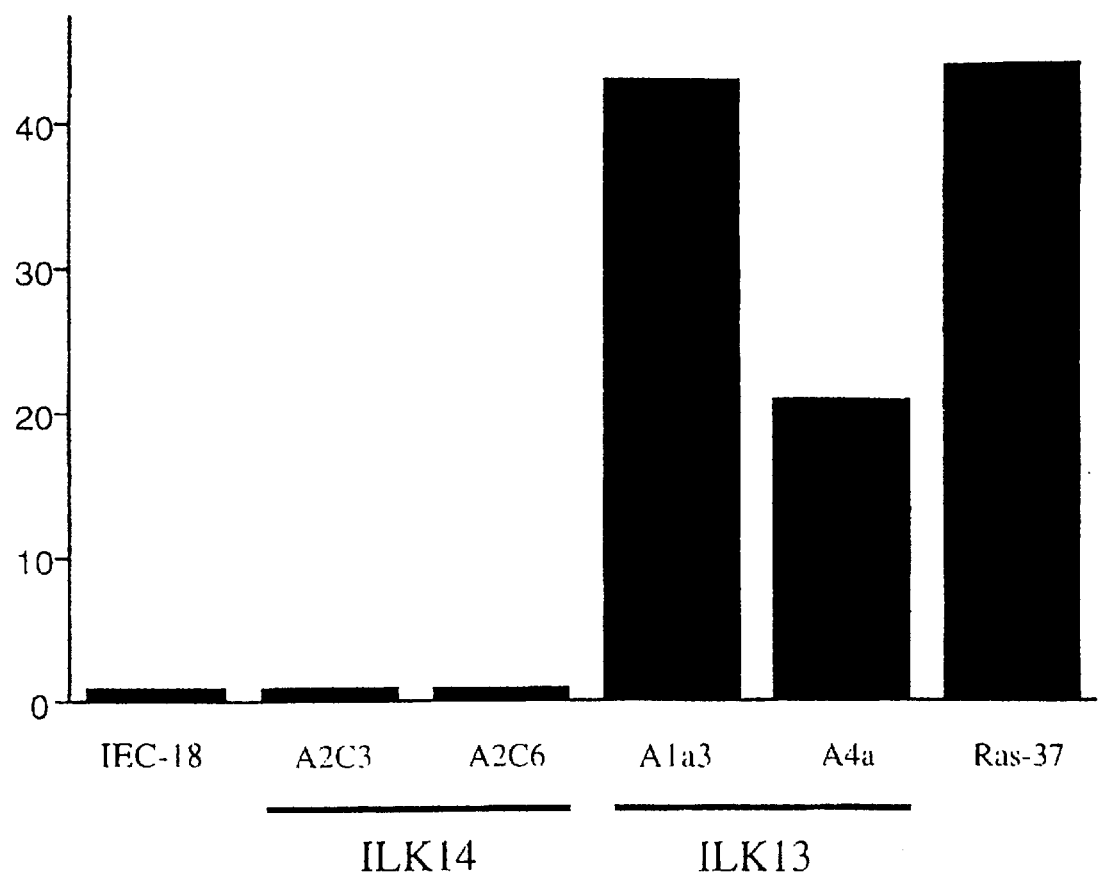

The fibronectin-dependent regulation of ILK kinase activity was tested. Plating of rat intestinal epithelial cells, IEC-18 on fibronectin reduced ILK phosphorylation of MBP in immune complex kinase assays, relative to cells plated on plastic, or kept in suspension (FIG. 4a). This fibronectin-dependent reduction of ILK activity was abrogated in IEC-18 cells expressing an activated H-ras allele, indicating that ras transformation disrupts ECM regulation of ILK activity in these cells. An expression vector containing the full-length ILK cDNA, pCMV-ILK, was stably transfected into IEC-18 cells. Twelve stable clones each, of pCMV-ILK and vector control transfectants, were selected and characterized for p59$^{ILK}$ expression levels. Two representative overexpressing subclones, ILK13-A1a3 and -A4a are illustrated (FIG. 4b). Overexpression of p59$^{ILK}$ disrupted the epithelial morphology of IEC-18 cells. ILK13 clones were more refractile, and grew on LN, FN and VN with a stellate morphology, in marked contrast to the typical, 'cobblestone' morphology of the parental and ILK14 cells (FIG. 4c). We plated the ILK13-A1a3 and -A4a subclones, the control transfectants, ILK14-A2C3 and -A2C6, and IEC-18 cells, on varying concentrations of the integrin substrates, laminin (LN), fibronectin (FN) and vitronectin VN). Adhesion of the ILK14 and IEC-18 cells was equivalent, whereas that of the overexpressing subclones was significantly reduced, on all these substrates (FIG. 4d). Immunoprecipitation analysis indicated that cell surface integrin expression was unaffected. The effect of p59$^{ILK}$ overexpression on anchorage-independent growth was examined by assaying the colony forming ability of ILK transfectants in soft agarose. In marked contrast to IEC-18 and transfectant controls, four independent p59$^{ILK}$ overexpressing subclones, ILK13- A4a, A1a3, A4d3 and A4C12, formed colonies in these assays (FIG. 4e). The proliferative rates of all of these clones on tissue culture plastic were equivalent to control rates.

FIG. 4 shows the modulation of ILK kinase activity by ECM components. a, ILK phosphorylation of MBP was assayed in ILK immune complexes, from lysates of IEC-18 intestinal epithelial cells which were harvested from tissue culture plastic and either kept in suspension, or replated on fibronectin, for 1 hour. A H-ras-transformed variant of IEC-18, Ras37 (transfected with Rasval12 in pRC/CMV vector), was assayed in parallel. The band shown is MBP. b, Expression levels of p59$^{ILK}$ in two representative clones of IEC-18 cells, transfected with an ILK expression construct (ILK13), two vector control clones (ILK14), and the parental IEC-18 cells are presented. The indicated amounts ($\mu$g/ lane) of whole cell RIPA lysates were run out on 10% SDS-PAGE gels, and p59$^{ILK}$ expression analyzed by Western blotting with affinity-purified 92-2 antibody. c, Representative p59$^{ILK}$ overexpressing clone ILK13-A4a, vector control clone ILK14-A2C3, and parental IEC-18 cells were plated on the ECM substrates LN, FN and VN for 1 hour, then fixed, stained with toluidine blue and photographed (40× mag). d, Adhesion of the ILK overexpressing clones to LN, FN and VN was quantified. Key: IEC-18 (black), ILK14-A2C6 (white), ILK13-A1a3 (dark grey), ILK13-A4a (light grey). Results are presented for 10 $\mu$g/ml substrate, and are expressed as % adhesion (+/−s. d.) relative to IEC-18, for each substrate. The serial concentrations of ECM showed similar reductions in adhesion of the ILK13 subclones, and ILK14-A2C3 adhesion was identical to that of ILK14-A2C6, on all three substrates. Immunoprecipitation of surface-biotinylated IEC-18, ILK13, and ILK14 subclones, with the anti-FNR and anti-VNR sera, confirmed there was no change in expression of $\alpha_5/\alpha_3\beta_1$ and $\alpha_v\beta_3/\beta_5$ integrin subunits in the p59$^{ILK}$ overexpressors. Data are representative of two independent experiments. e, Four ILK13, p59$^{ILK}$ overexpressing clones were plated in soft agarose, and assayed for colony growth after three (experiment 1) and two (experiment 2) weeks. Parent and vector control transfectants were also assayed, and the ras val12 transformed clone, Ras-37, was used as a positive control. Bars represent the mean of duplicate determinations. Maximum colonies in IEC-18 and ILK14 cells was 1/field.

The rat intestinal epithelial cell line IEC-18, and a variant of this line transfected with an activated H-rasval 12 allele, expressed from pRC/CMV, were grown on tissue culture plastic in 5% serum-containing medium, washed three times in minimum essential medium (MEM), and harvested with 5 mM EDTA. These were resuspended in 2.5 mg/ml BSA in MEM, and either kept in suspension, or plated on 10 μg/ml fibronectin-coated plates, for 1 hour at 37° C. NP-40 lysates (300 μg) of these cells were immunoprecipitated with affinity-purified 91-3, and immune complex kinase assays (MBP substrate) performed, as described above. IEC-18 were transfected with the expression vector pRC/CMV, containing Plac5 in the forward orientation relative to the CMV promotor. Stable clones were selected in G418, and subcloned through two rounds of limiting dilution. In all, twelve each of ILK and vector control transfectant subclones were isolated. Protein concentrations were determined using the Bradford reagent (Bio-Rad). Two $p59^{ILK}$ overexpressors, ILK13-A1a3 and ILK13-A4a, and two vector transfectant controls, ILK14-A2C3 and -A2C6, were analyzed for effects of ILK overexpression on cell adhesion to ECM substrates. Adhesion was quantified according to published methods. For colony formation assays $3 \times 10^5$ cells were plated in 35 mm wells, in 0.3% agarose, as described previously. Ras-37 were plated at $2 \times 10^3$/well. Colonies were counted and scored per field (d=1 cm) in duplicate wells, and defined as a minimum aggregate of 50 cells.

These results demonstrate that $p59^{ILK}$ overexpression in the IEC epithelial cells provides a growth advantage, in the absence of proliferative signals normally provided by adhesion.

The transduction of extracellular matrix signals through integrins influences intracellular ('outside-in') and extracellular ('inside-out') functions, both of which appear to require interaction of integrin cytoplasmic domains with cellular proteins.

The association of ILK with $\beta_1$ integrin subunits, and specific regulation of its kinase activity by adhesion to fibronectin, suggests that $p59^{ILK}$ is a mediator of integrin signaling. Thus the ankyrin repeat motif likely represents a protein interaction module specifying interactions of ILK with downstream, cytoplasmic or cytoskeletal proteins. Reduced ECM adhesion by the $p59^{ILK}$ overexpressing cells is consistent with our observation of adhesion-dependent inhibition of ILK activity, and suggests that $p59^{ILK}$ plays a role in inside-out integrin signaling. Furthermore the $p59^{ILK}$-induced, anchorage-independent growth of epithelial cells indicates a role for ILK in mediating intracellular signal transduction by integrins.

EXAMPLE 5

The Effect of Anti-ILK On Cell Migration

The role of ILK in cell motility has important implications for normal physiological processes such as inflammation and wound healing, as well as pathological conditions involving tumour invasiveness and metastatic tumour spread, or osteoporosis (bone is essentially an extracellular matrix secreted by osteoblast, or bone-forming cells, and this deposition can be modulated by integrin expression levels and function). Cell motility is a dynamic process, which is dependent on integrin-ECM interactions. The "on-off" switch function of protein kinases provides an ideal mechanism for the dynamic regulation of integrin affinity states for ECM substrates. The effect on cell migration of microinjecting highly specific anti-ILK antibodies (thereby inhibiting ILK function) into the cell's cytoplasm is assayed. These effects are assayed in endothelial cells plated on solid substrata, and are extended to include studies on cell migration through three-dimensional gels composed of ECM proteins.

EXAMPLE 6

Anti-Sense Oligonucleotides to Inhibit ILK Activity

The sequence of ILK cDNA provides information for the design and generation of synthetic oligonucleotides for "anti-sense" inhibition of ILK activity. This term derives from the strategy of employing a reverse complement of the coding, or sense strand of a specific messenger RNA, known as an anti-sense oligonucleotide (AO). By binding to its complementary mRNA, the AO inhibits translation of that mRNA into protein, thereby preventing normal protein accumulation in the cell. ILK AO derived from the ILK mRNA sequence closest to the presumptive translational start site, as defined in FIG. 1, will be tested, as this is predicted to provide the most successful reagent.

Regardless of the actual chemistry used to construct the AO, or modifications to an anti-ILK AO to improve its efficiency, the cDNA sequence of ILK provides the information for derivation of a specific AO. The cDNA sequence of ILK is also used to design oligonucleotide reagents, known as degenerate primers (due to the degeneracy of the genetic code), for use in polymerase chain reaction (PCR)-based screens for cDNAs structurally related to ILK. Similarly, the ILK cDNA is used to screen for related genes in a more conventional screen of genomic or cDNA libraries, by employing less stringent (i.e. milder) hybridization conditions during screening. In this way, distinct cDNA or DNA sequences significantly related to ILK (>50% nucleotide identity) can be isolated, and a family of ILK-related kinases identified in a non-random fashion.

EXAMPLE 7

Mapping of ILK Chromosomal Locus to Assess Imprinted Copies of Gene

High resolution mapping of the ILK chromosomal locus through fluorescent in situ hybridization (FISH) to metaphase (i.e. separated and identifiable) human chromosomes has placed the ILK gene on chromosome 11p15. FISH is known to those skilled in the art. High resolution mapping uses known marker genes in this region. Certain genes (e.g. insulin-like growth factor 2, IGF2) in the 11p15 region have been shown to be imprinted (i.e. preferentially expressed from either the maternally or paternally-derived chromosomes). This imprinting effectively provides a functional deletion or "knock-out" of one of the two inherited copies of a gene. Thus, mutation of the non-imprinted allele (copy) has a more profound outcome, since no compensatory activity is available from the imprinted allele. Also, 11p15 has been identified as a region subject to loss-of-heterozygosity, or LOH, in a subset of breast tumour patients. LOH results in the loss of one allele, for example by gene deletion, and is a mechanism underlying the contribution of a number of tumor suppressor genes to the development of various cancers (e.g. BRCA1 in breast, DCC in colon carcinoma, and RB1 in retinoblastoma). Thus ILK cDNA sequence is used to develop DNA reagents for the diagnosis and prognostic indications of a significant subset of breast cancers, and these reagents contribute to the molecular classification of such tumors. As mentioned above, the gene(s) on 11p15 contributing to some inherited cases of long QT syndrome are identified, and the candidacy of ILK as a causative gene for this cardiac condition, are evaluated by looking for alterations in ILK gene structure in families where 11p15 associations have been made.

EXAMPLE 8

Induction of in vivo Tumorigenesis by Overexpression of ILK

Overexpression of ILK down-regulates E-cadherin which is an important epithelial cell adhesion molecule mediating cell-cell communication/interaction. The loss of E-cadherin induced by overexpression of ILK in epithelial cells suggests that ILK may promote tumorigenicity in vivo. To test this, we injected cells expressing varying levels of ILK into athymic nude mice subcutaneously. Mice were inoculated subcutaneously with the cells expressing high (ILK13-A1a3 and A4a) or low (IEC-18 and ILK14-A2C3) levels of ILK ($10^7$ cells/mouse in PBS). The mice were monitored for tumor formation at the site of inoculation after three weeks. Tumors arose within three weeks in 50% to 100% of the mice injected with the ILK13 cells ($10^7$ cells/mouse) that overexpress ILK, whereas no tumors were detected in the mice that were injected with the same number of the IEC-18 or ILK14 cells expressing lower levels of ILK (Table 1). Thus, overexpression of ILK in these epithelial cells promotes tumor formation in vivo.

TABLE 1

Tumorigenicity of ILK Overexpressing IEC-18 Cells

| Cell Line | Number of Mice with Tumors at 3 weeks |
| --- | --- |
| IEC-18 | 0/6 |
| ILK14-A2C3 | 0/6 |
| ILK13-A1a3 | 6/6 |
| ILK13-A4a | 3/6 |

EXAMPLE 9

Increased Expression of ILK in Human Breast Carcinoma

Figure 5A:
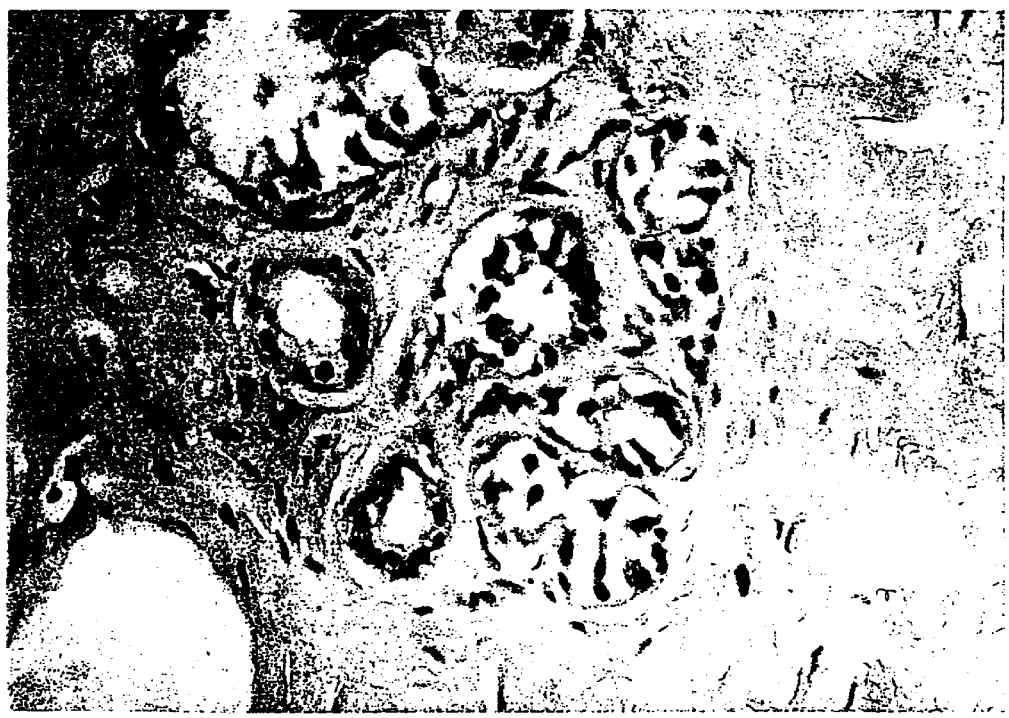
FIGS. 5a–5d Expression of ILK in human breast carcinomas. a, Normal region of breast tissue. b, Ductal carcinoma in situ. c,d, Invasive carcinoma.
Figure 5B:
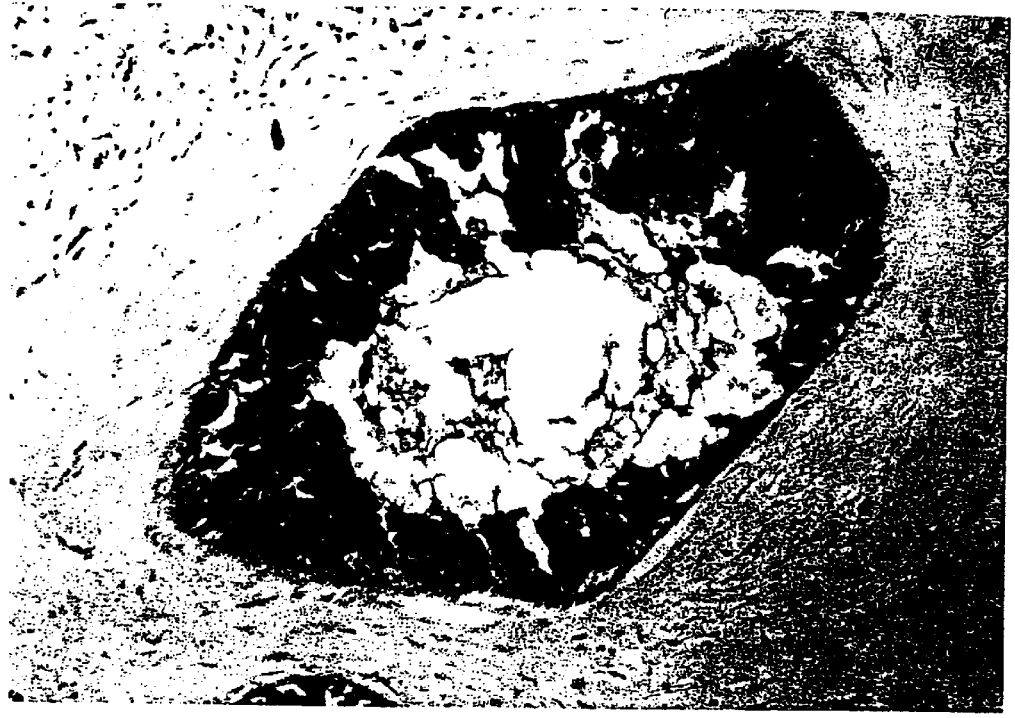
Figure 5C:
Figure 5D:
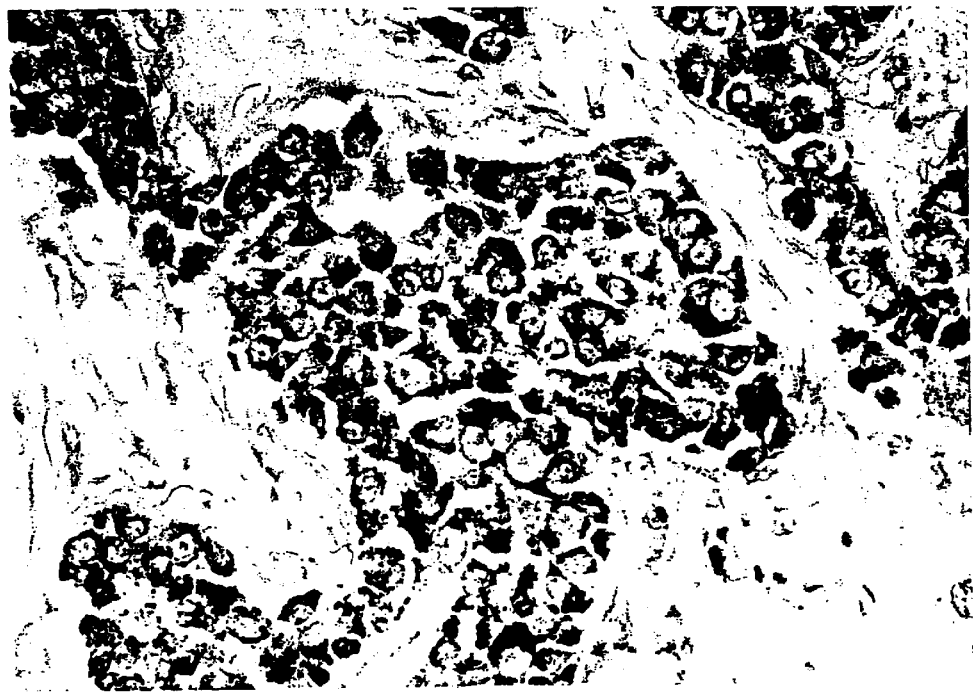

The expression of Integrin Linked Kinase in human breast carcinomas was determined by immunohistochemical staining of paraffin embedded sections from human breast cancer biopsies. Affinity purified anti-ILK polyclonal antibody was used followed by conjugated secondary antibody. The positive staining observed was completely abolished by absorption of the antibody to ILK-coupled sepharose beads. A total of 30 samples have been examined so far. In every case ILK expression levels are markedly elevated in tumor tissue compared to normal ducts and lobules. FIG. 5A shows a normal region showing well formed ducts with a single layer of epithelial cells. ILK staining is most prominent in epithelial cells. The stroma appears negative. FIG. 5B shows ductal carcinoma in situ (DCIS). Multiple cell layers are present with markedly elevated ILK staining in the tumor cells. Invasive carcinoma is depicted in FIGS. 5C and 5D. There is markedly elevated expression of ILK compared to the normal tissue shown in FIG. 5A.

EXAMPLE 10

Regulation of LEF-1 Expression and Complex Formation

Overexpression of ILK results in a downregulation of E-cadherin expression, formation of a complex between β-catenin and the HMG transcription factor, LEF-1, translocation of β-catenin to the nucleus, and transcriptional activation by this LEF-1/β-catenin complex. LEF-1 protein expression is rapidly modulated by cell detachment from the extracellular matrix, and that LEF-1 protein levels are constitutively upregulated upon ILK overexpression. These effects are specific for ILK, since transformation by activated H-ras or v-src oncogenes do not result in the activation of LEF-1/β-catenin. The results demonstrate that the oncogenic properties of ILK involve activation of the LEF-1/β-catenin signaling pathway via elevation of LEF-1 expression.

Overexpression of ILK in rat intestinal epithelial cells (IEC-18) induces a loss of epithelial morphology, characterized by a disruption of cell-cell adhesion and the acquisition of a fibroblastic morphology that includes enhanced fibronectin matrix assembly. This altered morphology is accompanied by the ability of the cells to progress through the cell cycle in an anchorage-independent manner and to form tumors in nude mice. To determine whether the loss of cell-cell adhesion was accompanied by an increased invasive phenotype, the invasiveness of IEC-18 parental cells and ILK-overexpressing (ILK-13) cells was tested in a collagen gel invasiveness assay. The data is shown in Table 2.

The ILK-13 cells are much more invasive than the parental and control transfected (ILK-14) cells that have been transfected with an ILK anti-sense cDNA construct. Collagen-gel invasion by epithelial cells is normally associated with an epithelial to mesenchymal transformation characterized by the down regulation of E-cadherin expression. Notably, the expression of E-cadherin protein is completely lost in ILK overexpressing cells (ILK-13), but is maintained in control transfected cells, reduced in IEC-18 cells transfected with activated H-ras cDNA, and greatly reduced in v-src transformed cells. In contrast, the steady-state levels of the expression of the intracellular E-cadherin binding protein, β-catenin, is unchanged by ILK overexpression and is similar in all IEC cell transfectants.

The subcellular localization of β-catenin was examined in these cells. In sharp contrast to the localization of β-catenin at the plasma membrane and at cell-cell adhesion sites in the parental IEC-18 and control transfected cell clones (A2c3 and A2c6), β-catenin is localized entirely in the nuclei of ILK overexpressing ILK-13 clones (A4a, A1a3). This ILK-induced nuclear localization of β-catenin is dependent on an active kinase, since overexpression of a kinase-deficient ILK (E359K) did not induce nuclear translocation of β-catenin which remains localized largely to the plasma membrane. Likewise, overexpression of kinase-deficient ILK also did not result in a loss of E-cadherin expression. The translocation of β-catenin to the nucleus is a specific property of ILK, since in IEC-18 cells transfected with activated H-ras or v-src oncogenes, β-catenin is not translocated to the nucleus, but is either localized to the plasma membrane or is expressed diffusely in the cytoplasm. Although these oncogenes also disrupt the epithelial morphology of IEC-18 cells and result in the downregulation of E-cadherin expression, the translocation of β-catenin to the nucleus is a property unique to ILK expression, suggesting that loss of E-cadherin expression and β-catenin nuclear translocation may be regulated differentially. Overexpression of ILK in mouse mammary epithelial cells also results in similar alterations in the phenotypic properties described above for the IEC-18 cells.

Translocation of β-catenin to the nucleus can be induced by the activation of the Wnt signaling pathway, which initially results in an elevation of free cytosolic β-catenin due to decreased degradation. Alternatively, loss of expression or mutations in the tumor suppressor protein APC and certain mutations in the β-catenin gene lead to cytosolic β-catenin stabilization and nuclear translocation. The nuclear translocation of β-catenin is associated with complex formation between β-catenin and members of the HMG transcription factors, LEF-1/TCF which then activate (or silence) transcription of target genes. Since the steady state levels of β-catenin were not changed by ILK overexpression "uncomplexed" β-catenin levels were measured, as determined by binding to a cytoplasmic domain peptide of E-cadherin. "Uncomplexed" pools of β-catenin in ILK overexpressing clones were found to be low and unaltered compared to IEC-18 cells or control ILK 14 clones. This indicates that most β-catenin is likely complexed with nuclear components such as transcription factors and DNA. In contrast, free β-catenin pools in Ras and Src transformed cells were high consistent with decreased E-cadherin expression and indicating disruption of E-cadherin-β-catenin interaction. However, the increased free pools of β-catenin did not result in nuclear translocation of β-catenin.

The expression levels of LEF-1, a member of the family of HMG transcription factors that bind β-catenin, were measured. The expression of LEF-1 is dramatically higher in six independent ILK expressing ILK-13 cell clones as compared with six independent control transfected ILK-14 clones, as well as 2 activated H-ras transfected and v-src transfected IEC-18 clones. E-cadherin expression is lost in all 6 ILK-13 cell lines. Transient induction of ILK expression using an ecdysone inducible ILK construct also resulted in an increase of LEF-1 expression. As expected, the increased levels of LEF-1 and the nuclear translocation of β-catenin are associated with enhanced complex formation between LEF-1 and β-catenin in the ILK overexpressing cells.

LEF-1 is a transcription factor that is by itself, unable to stimulate transcription from multimerized binding sites, however in association with β-catenin, LEF1/TCF proteins can augment promoter activity from multimerized binding sites. Transcriptional activation from a TCF/β-catenin responsive promoter construct was examined in ILK-overexpressing cells and control kinase- deficient ILK expressing cells. High promoter activity was observed in ILK-overexpressing cells and the extent of transcriptional activation was reduced with promoter constructs containing mutations in the multimerized LEF-1/TCF binding sites. Moreover, nuclear extracts were analyzed from ILK-overexpressing cell clones and from cell clones transfected with an anti-sense or kinase-deficient ILK cDNA to identify proteins that bind the LEF/TCF binding site. The abundance of a nuclear factor in ILK-overexpressing cells That displays the same binding site specificity, immunoreactivity and electrophoretic mobility as LEF-1, was found to be markedly enhanced relative to the unrelated DNA-binding protein Oct-1.

ILK binds to the cytoplasmic domain of $\beta_1$ and $\alpha_3$ integrin subunits, and its kinase activity is downregulated upon cell adhesion to extracellular matrix (ECM) proteins. Overexpression of constitutively activated ILK overcomes this regulation of ILK activity by integrin occupation and results in decreased cell adhesion to ECM-protein. Cell adhesion to ECM suppresses LEF-1 expression, which is rapidly, but transiently, elevated upon cell detachment in ILK-14 and ILK13 cells. However in ILK overexpressing ILK-13 cells the elevation in LEF-1 levels are more robust and are maintained at high levels for as long as 16 hours in suspension. Furthermore, LEF-1 levels are also higher in adherent ILK-13 cells compared to ILK-14 cells.

These data indicate that ILK overexpression overcomes the regulation of LEF-1 expression by adhesion-deadhesion, and that the maintenance of constitutively high levels of LEF-1 result in enhanced complex formation between LEF-1 and β-catenin, translocation of β-catenin to the nucleus, and transcriptional activation of responsive genes. Since TCF/β-catenin has been shown to induce transcription of genes encoding homeobox proteins that regulate mesenchymal genes eg. Siamois in Drosophila, this pathway is likely to mediate the observed epithelial to mesenchymal transformation, as well as the oncogenic properties of ILK in these intestinal epithelial cells, since constitutive activation of TCF/β-catenin is oncogenic in human colon carcinomas. The data presented here also suggest a connection between the expression of E-cadherin and the signaling properties of β-catenin in mesenchymal induction in ILK transformed cells, in agreement with the work of others that E-cadherin can antagonize β-catenin signaling, although the loss of E-cadherin expression does not always correlate with nuclear β-catenin translocation e.g. in the v-src transformed cells.

An additional pathway is demonstrated to that by activated Wnt-1 leading to increased LEF-1/β-catenin complex formation and transcriptional activation. These data also corroborate previous work showing that overexpression of LEF-1 can work independently of Wnt to enhance LEF-1-β-catenin complex induced transcription. Here it is shown that in contrast to the effects of Wnt-1, activated ILK can dramatically induce the formation and nuclear translocation of LEF-1/β-catenin complexes without a corresponding increase in the free pool of β-catenin. This ILK-regulated pathway may be modulated via cell adhesion to ECM, but can be constitutively activated by ILK overexpression.

Methods

Cells and cell culture. IEC-18 rat intestinal epithelial cells were stably transfected with a mammalian vector incorporating ILK to produce clones overexpressing wt ILK in the sense orientation (ILK-13) or antisense orientation (ILK-14), or to produce a kinase-deficient form of ILK (IEC-18GH31RH) described below. IEC-18 cells were also stably transfected to overexpress H-ras (Ras 33, Ras 37) (Buick et al. (1987) Exp. Cell. Res. 170:300–309), and v-src (Src2, Src4) (Filmus et al. (1988) Mol. Cell. Biol. 8:4243–4249). Cells were grown in d-MEM containing 5% FCS, 2 mm L-glutamine, glucose (3.6 mg/ml), insulin (10 ug/ml), and G418 (40 ug/ml) was added to transfected cells to maintain selection pressure.

Site directed mutagenesis of ILK kinase domain. Mutations were introduced into wt ILK-cDNA with the Promega Altered Sites II System (Promega, Madison Wis.). Mutant oligomers (with the altered nucleotide underlined) were used to change lysine at position 220 to an arginine (K220R, (SEQ ID NO:9) 5' CCTTCAGCACC CTCACGACMTGTCATTGCCC 3') and glutamic acid at position 359 to lysine (E359K, (SEQ ID NO:10) 5' CTG-CAGAGCTTTGGGGGCTACCCAGGCAGGTG 3'). Mutant clones were confirmed by dideoxy sequencing and subcloned into pGEX4T-1 GST fusion vector (Pharmacia, Piscataway N.J.) to express GST-ILK in E. coli (BL21-DE3) and into pcDNA3 (Invitrogen, San Diego, Calif.) to stably transfect kinase-deficient ILK into the IEC-18 cell line (IEC-18GH31RH containing the E359K mutation).

Inducible expression of ILK. Full length wt ILK cDNA (1.8 Kb) was subcloned into the Ecdysone-inducible expression vector pIND (Invitrogen, San Diego, Calif.) and 10 ug were transiently co-transfected with 10 ug of the complementary regulator vector pVgRXR into subconfluent cells growing in 6 well plates with 20 ul of Lipofectin (Gibro-BRL, Gaithersburg, Md.). ILK expression was induced 6 hrs later with the addition of 1 uM muristerone A.

Western blotting and immunoprecipitation. Cells were lysed for 10 minutes on ice in NP-40 lysis buffer (1% NP40, 50 mM Hepes, pH 7.4, 150 mM NaCl, 2 mM EDTA, 2 mM PMSF, 1 mM Na-o-vanadate, 1 mM NaF, 10 ug/ml aprotinin, 10 ug/ml leupeptin). Extracts were centrifuged with the resulting supernatants being the cell lysate used in assays. Lysates were electrophoresed through SDS-PAGE and transferred to Immobilon-P membranes (Millipore, Bedford, Md.). Antibodies used to probe Western blots were: rabbit anti-ILK, monoclonal anti-E-cadherin and monoclonal anti-β-catenin (Transduction Labs, Lexington, Ky.), and rabbit anti-LEF-1 (Travis et al. (1991) *Genes & Development* 5:880–894). Bands were visualized with ECL chemiluminescent substrate (Amersham, Buckinghamshire, England). For immunoprecipitation, NP-40 lysates were rotated with primary antibody ON at 4° C., then rotated with Protein G-Sepharose (Pharmacia, Uppsala, Sweden) for 2 hrs at RT. Beads were pelleted, boiled in electrophoresis sample buffer (non-reducing), centrifuged and supernatants were electrophoresed. Protein concentrations were determined by the Bradford assay (Bio-Rad, Hercules, Calif.).

Invasion assay. Confluent cells were trypsinized and $7.5 \times 10^4$ cells in 1.5 ml of complete medium were seeded onto 1.5 ml of a three dimensional collagen gel in a 35 mm tissue culture dish (Montesano et al. (1985) Cell 42:469–477). Upon reaching confluence (3 days), the cultures were incubated for a further 4 days, then fixed in situ with 2.5% glutaraldehyde in 100 mM cacodylate buffer (pH 7.4), and photographed at different planes of focus. Invasion was quantitated by counting the number of cells which had migrated below the surface of the collagen gel. Five randomly selected fields measuring 1.0 mm×1.4 mm were photographed at a single level beneath the surface monolayer using a 10× phase contract objective.

Indirect immunofluorescence. Cells were grown on cover slips, washed with PBS, fixed in 4% paraformaldehyde in PBS for 12 minutes, washed with PBS, permeabilized in 0.1% Triton X-100 in PBS for 10 minutes, blocked with 4% BSA in PBS for 30 minutes at RT, incubated with rabbit anti-β-catenin (Hulsken et al. (1994) J. Cell Biol. 127:2061–2069) diluted 1:400 in 0.1% Triton X-100 for 60 minutes at 37° C., washed with PBS, incubated with rhodamine conjugated goat anti-rabbit IgG (Jackson ImmunoResearch, West Grove, Pa.) diluted 1:50 in 0.1% Triton X-100 for 30 minutes at 37° C., washed with PBS, then mounted onto a slide with Slow-Fade Antifade (Molecular Probes Inc., Eugene, Oreg.). Cells were viewed at 100 fold magnification using a Zeiss Axiovert 135 fluorescence microscope.

Reporter gene assay. Cells were transiently transfected with 0.3 ug of a luciferase reporter gene construct containing a series of optimal or mutated LEF-1/TCF binding sites (Korinek et al. (1997) Science 275:1784–1787), along with 0.05 ug of a CAT gene construct containing a ribosomal promoter (Hariharan et al. (1989) Genes & Development 3:1789–1800) to control for transfection efficiency. Extracts were prepared and assayed 48 hours after transfection.

Electrophoretic mobility shift assay. Twenty μg of nuclear extract were incubated with 1 fmole of $^{32}$P-labeled duplex oligonucleotide probe specific for LEF-1, in 20 μl of binding buffer containing 200 ng poly[d(I-C)], 400 ng salmon sperm DNA, and electrophoresed through a 5% native polyacrylamide gel (Travis et al. (1991) Genes and Development 5:880–894). For DNA competition, an 800-fold molar excess of oligonucleotide containing a specific LEF-1 binding site or a non-specific EBF-binding site (Hagman et al. (1991) EMBO J. 10:3409–3417) was included in the DNA-binding reaction. For antibody addition, 1 ul of polyclonal anti-LEF-1 antibody or 1 ul of monoclonal anti-β-catenin antibody (Transduction Labs, Lexington, Ky.) were used.

TABLE 2

INVASION OF COLLAGEN GELS

| Cell Line | Invading cells/field |
|---|---|
| IEC-18 | 10 +/− 0.87 |
| ILK14/A2c | 67.8 +/− 1.32 |
| ILK13/A1a | 326.73 +/− 2.61 |
| ILK-13/A4a | 83.6 +/− 4.68 |

After seeding $7.5 \times 10^4$ cells, the number of invading cells in 5 photographic fields from 3 separate experiments (total of 15 fields/cell line) were counted. Results are given as the mean number of invading cells±SEM. *p<<0.01 between ILK13/A1a3 compared to IEC-18 and ILK-14 cells (Students unpaired t=test).

EXAMPLE 11

Regulation of Fibronectin Matrix Assembly, E-cadherin Expression and Tumorigenicity A common feature of many oncogenically transformed cells is that they lose the ability of assembling a fibronectin (Fn) matrix. However, exceptions to the rule of neoplastic cells lacking Fn matrix clearly exist. For example, Fn matrix assembly is dramatically enhanced in hairy cell leukemia cells. The specific phenotype (inhibition or stimulation of Fn matrix assembly) is probably determined by the origin of the neoplastic cells and the initial target of the oncogenic transformation. Because Fn matrix has a major impact on cell adhesion, migration, cell growth and cell differentiation, an understanding of the molecular mechanism by which cells control Fn matrix assembly may provide important information on tumorigenicity and may lead to new ways of controlling tumor growth.

Binding of Fn by specific integrins is critical in initiating Fn matrix assembly. Fn fragments containing the RGD-containing integrin binding site or antibodies recognizing the integrin binding site inhibit Fn matrix assembly. In addition, antibodies to $\alpha_5\beta_1$ integrin reduce the deposition of Fn into extracellular matrix by fibroblasts. In addition to $\alpha_5\beta_1$ integrin, members of the $\beta_3$ integrins ($\alpha_{IIb}\beta_3$ and $\alpha_v\beta_3$) also initiate Fn matrix assembly, although some of the other Fn binding integrins such as $\alpha_4\beta_1$ or $\alpha_v\beta_1$ do not. The ability of cells to use multiple integrins to support Fn matrix assembly provides the cells with a versatile mechanism for control of Fn matrix assembly. It may also explain why certain cells, such as fibroblastic cells derived from $\alpha_5$ integrin null mutant embryos, assemble a Fn matrix in the absence of $\alpha_5\beta_1$. The primary role of $\alpha_5\beta_1$ in Fn matrix assembly appears to involve initiating the assembly, as Fn mutants lacking the $\alpha_5\beta_1$ integrin binding site could not be assembled into Fn matrix unless in the presence of native Fn.

Activation of specific Fn binding integrins, either by mutations at the integrin cytoplasmic domains or using activating antibodies, dramatically stimulates Fn matrix assembly. The ability of a cell to assemble a Fn matrix is not only controlled by the types of integrins it expresses but also regulated by the Fn binding activity of the integrins. The extracellular ligand binding affinity of integrins can be controlled from within the cells (inside-out signaling).

Integrin-linked kinase (ILK) may be involved in regulating Fn matrix assembly. ILK binds to the cytoplasmic domains of both $\beta_1$ and $\beta_3$ integrins, and phosphorylates the $\beta_1$ cytoplasmic domain in vitro. Overexpression of ILK in epithelial cells dramatically stimulated integrin-mediated Fn matrix assembly, down-regulated E-cadherin, and induced tumor formation in vivo. The data identify ILK as an important regulator of pericellular Fn matrix assembly, and suggest a critical role of this integrin-linked kinase in cell-cell interactions and tumorigenesis.

Reagents

All organic chemicals were of analytic grade and were obtained from Sigman Chemical Co. (St. Louis, Mo.) or Fisher Scientific Co. (Pittsburgh, Pa.) unless otherwise specified. Media for cell culture were from Gibco Laboratories (Grand Island, N.Y.). Fetal bovine serum was from HyClone Laboratories, Inc. (Logan, Utah). Polyclonal rabbit anti-$\beta_5$ integrin cytoplasmic domain antibody AB47 was generated using a synthetic peptide representing the membrane distal region of the $\alpha_5$ integrin cytoplasmic domain ((SEQ ID NO:11) LPYGTAMEKAQLKPPATSDA). Polyclonal rabbit anti-Fn antibody MC54 was raised against purified plasma Fn and purified with a protein A-Sepharose affinity column (Wu et al. (1993) *J. Biol. Chem.* 268:21883–21888). Polyclonal rabbit anti-29 kDa fragment of Fn antibody was raised against the aminoterminal 29 kDa fragment of Fn and was further purified using Sepharose beads coupled with the 29 kDa fragment of Fn (Limper et al. (1991) *J. Biol. Chem.* 266:9697–9702). Anti-ILK polyclonal antibody 91-4 was prepared in rabbits as described previously (Hannigan et al. (1996) *Nature* 379:91–96). Monoclonal hamster anti-rat $\alpha$5 integrin antibody (HM$\alpha$5-1) and mouse anti-rat $\beta_3$ integrin antibody (F11) were from PharMingen (San Diego, Calif.). Monoclonal mouse anti-vinculin antibody (hVIN-1) and purified rabbit IgG were purchased from Sigma (St. Louis, Mo.). The Fn fragments (110 kDa RGD containing integrin binding fragment, the 20 kDa and 70 kDa amino terminal fragments, and the 60 kDa gelatin binding were prepared as previously described (Quade and McDonald (1988) *J. Biol. Chem.* 263:19602–19609).

cDNA Vectors, Transfection and Cell Culture. Rat intestinal epithelial cells (IEC-18) were maintained in $\alpha$-MEM medium (Gibco Laboratories, Grand Island, N.Y.) supplemented with 5% FBS (Atlanta Biologicals, Norcross, Ga.), 3.6 mg/ml gluconse, 10 $\mu$g/ml insulin and 2 mM glutamine. The pRC/CMV and metallothionein promoter (MT) driven expression vectors containing sense and anti-sense full length ILK cDNA sequences were generated as described above. The expression vectors were transfected into IEC-18 cells using calcium phosphate and the transfected cells were selected with G418 as described. The expression of human ILK in IEC-18 cells transfected with the MT-ILK expression vectors (MT-ILK) was induced by growing the cells in $\alpha$-MEM medium containing 125 $\mu$M ZnSO$_4$ and 2.5 $\mu$M CdCl$_2$ for 24 to 48 hours. The kinase-inactive ILK mutant (GH31R) was generated by a single point mutation (E→K) at amino acid residue 359 within the kinase subdomain VIII using the Promega Altered Site II in vitro Mutagenesis System. The mutated DNA was cloned into a pGEX expression system (Pharmacia), and expressed as a GST fusion protein. Kinase assays were carried out using the recombinant protein as described above and the results showed that the $E^{359}$→K point mutation completely inactivated the kinase activity. The cDNA encoding the kinase-inactive mutant was cloned into a pcDNA3 expression vector (Invitrogen), transfected into IEC-18 cells and stable transfectants were selected.

Determination of ILK, E-cadherin and $\beta_1$ integrin levels. The cellular levels of ILK and E-cadherin were determined by immunoblot using an affinity-purified polyclonal rabbit anti-ILK antibody 91-4, and an anti-E-cadherin antibody (Upstate Biotechnologies, Inc.). The cell surface expression of $\alpha_5\beta_1$ integrins was estimated by immunoprecipitation of surface biotinylated cell lysates with a polyclonal rabbit anti-$\alpha_5\beta_1$ antibody.

Immunofluorescent Staining. Fn matrix assembly was analyzed by immunofluorescent staining of cell monolayers (Wu et al. (1995) *Cell* 83:715–724). Cells were suspended in the $\alpha$-MEM medium containing 5% FBS and other additives as specified in each experiment. Cells were plated in 12-well HTC$^R$ slides (Cel-Line, Inc., Newfield, N.J.; 50 $\mu$l/well) at a final density of 2×10$^5$ cells/ml and cultured in a 37° C. incubator under a 5% CO$_2$-95% air atmosphere. Cells were fixed with 3.7% paraformaldehyde, and staining with the polyclonal rabbit anti-Fn antibody MC54 (20 $\mu$g/ml) and Cy3-conjugated goat anti-rabbit IgG antibodies (Jackson ImmunoResearch Lab, Inc, West Grove, Pa.; 2.5 $\mu$g/ml). Stained cell monolayers were observed using a Nikon FXA epifluorescence microscope and representative fields were photographed using Kodak T-Max 400 or Ektachrome 1600 direct positive slide film. To obtain representative images, exposure times for different experimental conditions were fixed, using the positive, e.g., matrix forming cells, as the index exposure length.

In double staining experiments, 3.7% paraformaldehyde fixed cells were permeablized with 0.1% Triton X-100 in TBS containing 1 mg/ml BSA. The cells were then incubated with primary antibodies from different species as specified in each experiment. After rinsing, the bound primary antibodies were detected with species-specific Cy3- and FITC-conjugated secondary antibodies. Stained cell monolayers were observed using a Nikon FXA epifluorescence microscope equipped with Cy3 and FITC filters.

For inhibition studies, ILK13-A4a cells that overexpress ILK were plated in 12-well HTC$^R$ slides in the $\alpha$-MEM medium containing 5% FBS and other additives as specified (2 $\mu$M anti-29 kDa Fn fragment antibody, 2 $\mu$M rabbit control IgG, or 4.2 $\mu$M of one of the following Fn fragments: 110 kDa RGD containing integrin binding fragment of Fn, 70 kDa aminoterminal fragment of Fn or 60 kDa gelatin binding fragment of Fn). The cells were cultured for four hours, and then fixed and stained with the polyclonal rabbit anti-Fn antibody and the Cy3-conjugated goat anti-rabbit IgG antibodies as described above.

Isolation and Biochemical Characterization of Extracellular Matrix Fn. To isolate and biochemically characterize extracellular matrix Fn, the cells were cultured in 100 mm tissue culture plates (Corning, Inc., Corning, N.Y.) in $\alpha$-MEM medium supplemented with 5% FBS, 2 mM L-glutamine, 3.6 mg/ml glucose, 10 $\mu$g/ml insulin and other additives as specified in each experiment for two days. Then the cell monolayers were washed three times with PBS containing 1 mM AEBSF and harvested with a cell scraper. The extracellular matrix fraction was isolated by sequential extraction of the cells with (1) 3% Triton X-100 in PBS containing 1 mM AEBSF; (2) 100 $\mu$g/ml DNase I in 50 mM Tris, pH 7.4, 10 mM MnCl$_2$, 1 M NaCl, 1 mM AEBSF and (3) 2% deoxycholate in Tris, pH 8.8, 1 mM AEBSF (Wu et al., supra.) Fn in the deoxycholate insoluble extracellular matrix fraction was analyzed by immunoblot with polyclonal rabbit anti-Fn antibody MC54 and an ECL detection kit as previously described (Wu et al. (1995) *J. Cell Sci.* 108:821–829).

Colony formation in soft agar. ILK13-A1a3 cells that overexpress ILK (3×10$^5$/well), and Ras-37 cells that overexpress H-RasVal12 (2×10$^3$/well) were plated in 35 mm wells, in 0.3% agarose and assayed for colony growth after three weeks as described above. Fn fragments were incorporated in the agar at the final concentrations indicated.

Tumor formation in athymic nude mice. IEC-18, ILK14, or ILK13 cells were resuspended in PBS and inoculated subcutaneously into athymic nude mice ($10^7$/mouse). Six mice were inoculated per cell line. In situ tumor formation was assessed after 3 weeks.

Tyrosine Phosphorylation of $p125^{FAK}$ in ILK cells. ILK13-A1a3 and ILK14-A2C3 cells growing in monolayer culture were harvested using 5 mM EDTA/PBS (Phosphate Buffered Saline, pH 7.6) and the cells were washed twice in PBS. Cells were resuspended in serum free medium and then transferred to plain tissue culture plates (Nunc), tissue culture plates precoated with 10 µg/ml Fn (Gibco/BRL) or maintained in suspension. For the suspension control cells were kept in 50 ml rocker tube. After 1 hour incubation at 37° C. in 5% $CO_2$ cell monolayer (for the adherent controls) and cell pellet (for the suspension controls) were washed twice in ice-cold PBS and lysed in NP-40 lysis buffer (1% NP-40; 150 mM NaCl; 50 mM Tris, pH 7.4; 1 mM EDTA, 1 mM PMSF, 0.2 U/ml aprotonin, 2 µg/ml leupeptin and 1 mM Sodium Vanadate). FAK was immunoprecipitated from 400–500 µg of total cell extract using 4 µg mouse monoclonal anti-$p125^{FAK}$ antibody and Protein A-Agarose conjugate (UBI). Immune complexes were washed three times in lysis buffer, boiled in SDS-PAGE sample buffer and run on a 7.5% gel. Resolved proteins were transferred to Immobilon-P (Millipore) and membrane blocked in 5% BSA (Sigma) in TBST (0.1% Tween-20 in Tris Buffered Saline, pH 7.4). Tyrosine-phosphorylated FAK was detected using the RC20H recombinant antibody (HRP-conjugate, Transduction) and ECL detection system (Amersham).

RESULTS

Stimulation of Fn matrix assembly by ILK. To determine whether ILK plays a role in regulation of Fn matrix assembly, the ability of cells expressing different levels of ILK to assemble a Fn matrix was analyzed. IEC-18 rat intestinal epithelial cells assembled a small amount of Fn matrix consisting of mostly short fibrils. ILK13-A1a3 cells, which were isolated from the IEC-18 cells stably transfected with a pRC/CMV expression vector containing full length ILK coding sequence, express a much higher level of ILK than the parental IEC-18 cells. The ILK overexpressing ILK13-A1a3 cells assembled an extensive Fn matrix resembling that formed by fibroblasts, whereas control transfectants (ILK14-A2C3), which express a similar level of ILK as the parental IEC-18 cells, assembled a small amount of Fn matrix that is indistinguishable from that of the IEC-18 cells fibroblasts. To exclude the possibility that the observed effect depends on a specific clone, ten additional cell lines were analyzed that were independently isolated from the cells transfected with the pRC/CMV-ILK expression vector (ILK13-A4a, A1d11, A4c, A4c3 and A4i) or the control vector (ILK14-A2C6, A2a3, A2g3, A2g8 and A3a1). Fn matrix assembly was dramatically increased in all six ILK-overexpressing cell lines (Table 3). On the other hand, all six control cell lines assembled a low level of Fn matrix resembling that of the parental IEC-18 cells. In marked contrast to overexpression of ILK, overexpression of an oncogenic H-Ras mutant in which the twelfth amino acid residue is mutated (H-RasVal12) in the IEC-18 cells abolished the assembly of Fn fibrils.

TABLE 3

Fn matrix assembly by cells expressing different levels of ILK

| Cell Line | ILK Expression level | Extracellular Fn matrix level |
|---|---|---|
| ILK13 (A1a3, A4a, A1d11, A4c | High (wild type ILK) | High |
| ILK14 (A2C6, A2C3, A2a3, A2g3, A2g8 and A3a1), IEC-18, MT-ILK6 (E2) | Low (wild type ILK) | Low |
| GH31RH | High (kinase-inactive mutant) | Low |

The ILK 13 cell lines were independently isolated from IEC-18 rat intestinal epithelial cells that were stably transfected with a pRC/CMV expression vector containing full length ILK coding sequence and they express a much higher level of ILK than the parental IEC-18 cells. The ILK 14 cells were control transfectants (41). The MT-ILK1 (IIB8) cells were isolated from IEC-18 cells transfected with the sense ILK expression vector (MT-ILK1). The MT-ILK6 (E2) cells were isolated from IEC-18 cells transfected with the anti-sense ILK expression vector (MT-ILK6). The GH31R cells were isolated from IEC-18 cells transfected with a pCDNA3 expression vector encoding a ILK kinase-inactive mutant in which glutamic acid residue 359 was replaced with a lysine residue. The relative ILK expression levels were based on immunoblot analysis with anti-ILK antibodies.

To further confirm a regulatory role of ILK in Fn matrix assembly, IEC-18 cells were transfected with expression vectors containing full length ILK cDNA in the forward (sense) or the reverse (anti-sense) orientation that were under the control of metallothionein promoter (MT). The MT-ILK1 (IIB8) cells, which were derived from the IEC-18 cells transfected with the sense ILK expression vector, expressed more ILK than the MT-ILK6 (E2) cells that were derived from the IEC-18 cells transfected with the anti-sense ILK expression vector. The difference in ILK expression was maximized when the cells were grown in the presence of $Zn^{++}$ and $Cd^{++}$. Consistent with a critical role of ILK in Fn matrix assembly, the ILK overexpressing MT-ILK1 (IIB8) cells exhibit a much high Fn matrix assembly than the MT-ILK6 (E2) cells that have a much lower level of ILK. Thus, overexpression of ILK, either driven by a CMV promoter or driven by a metallothionein promoter, stimulates Fn matrix assembly.

Involvement of integrin-linked kinase activity in the cellular regulation of Fn matrix assembly. To test whether the kinase activity is involved in the stimulation of Fn matrix assembly by ILK, a kinase-inactive ILK mutant (GH31R) was overexpressed in the IEC-18 cells. Unlike cells overexpressing the wild type ILK, cells overexpressing the kinase-inactive ILK mutant did not assemble an increased amount of Fn into the extracellular matrix (FIG. 1D). Thus, the kinase activity is critical in the cellular signal transduction leading to the up-regulation of Fn matrix assembly.

Biochemical characterization of Fn matrix assembled by cells overexpressing ILK. The Fn matrix deposited by fibroblastic cells is characterized by insolubility in sodium deoxycholate. To determine whether Fn matrix induced by overexpression of ILK in the epithelial cells shares this characteristic, the cell layers were extracted with 2% sodium deoxycholate and the insoluble matrix fractions analyzed by immunoblotting. The cells overexpressing ILK (A1a3, A4a and IIB8 ) assembled much more Fn into the deoxycholate insoluble matrix than the cells that express relatively low level of ILK (A2C6, A2C3, and E2). By contrast, cells overexpressing H-RasVal12 failed to deposit detectable amount of Fn into the detergent insoluble matrix (H-Ras). These results are consistent with the immunofluorescent staining data. Taken together, they provide strong evidence supporting an important role of ILK in regulation of Fn matrix assembly.

Participation of the RGD containing integrin-binding domain and the amino terminal domain of Fn in ILK stimulated Fn matrix assembly. Integrin-mediated Fn matrix assembly requires at least two discrete portions of Fn, the RGD containing integrin-binding domain and the aminoterminal domain. To determine whether these domains also participate in Fn matrix assembly induced by overexpression of ILK, the 110 kDa RGD containing fragment, the 70 kDa aminoterminal domain of Fn, and an antibody against the amino terminal domain of Fn (anti-29 kDa) were utilized. Both the antibody and the Fn fragments decreased the Fn fibril formation induced by ILK. The inhibition was specific, as neither irrelevant rabbit IgG nor a 60 kDa Fn Fragment lacking the amino terminus inhibited the Fn matrix assembly. Thus, both the RGD containing integrin-binding domain and the amino terminal domain of Fn are involved in Fn matrix assembly promoted by overexpression of ILK, suggesting a role of Fn-binding integrins in this process.

Co-distribution of $\alpha5\beta1$ integrin and Fn matrix in cells overexpressing ILK. To begin to identify which Fn-binding integrin mediates Fn matrix assembly induced by overexpression of ILK, cells overexpressing ILK were stained with a hamster monoclonal anti-rat $\alpha5$ integrin antibody and a rabbit polyclonal anti-Fn antibody. The double-staining experiments showed that $\alpha_5\beta_1$ integrin was co-localized with Fn fibrils in A1a3 cells that overexpress ILK. In contrast, staining of the cells with an anti-rat $\beta_3$ integrin antibody revealed no distinctive staining. These results suggest that $\alpha_5\beta_1$ integrin, but not $\beta_3$ integrins, participate in the Fn matrix assembly induced by overexpression of ILK.

In contrast to cells that overexpress ILK, cells expressing a lower level of ILK (A2C6) have fewer clusters of $\alpha_5\beta_1$ integrin that could be detected by immunofluorescent staining, although these cells express the same level of cell surface $\alpha_5\beta_1$ integrin as the cells overexpressing ILK. Moreover, in marked contrast to A1a3 cells that overexpress ILK, many of the structures containing $\alpha_5\beta_1$ integrin in the A2C6 cells lacked detectable Fn, indicating that overexpression of ILK enhances the binding of Fn to $\alpha_5\beta_1$ integrin.

Effect of ILK overexpression on the formation of focal adhesion and matrix contacts. Cell adhesion to extracellular substrates is mediated by transmembrane complexes termed focal adhesions which contain integrin, vinculin and other cytoskeletal proteins. A connection between extracellular Fn and the intracellular actin cytoskeleton involving the integrin β cytoplasmic domain is required for the assembly of Fn fibrils. A2C3 cells that express low levels of ILK formed abundant focal adhesions visualized by staining with an anti-vinculin antibody. However, only a small amount of $\alpha_5\beta_1$ integrin and Fn were co-localized with the focal adhesions in A2C3 cells. Overexpression of ILK promoted co-localization of $\alpha_5\beta_1$ integrin and Fn with vinculin. Thus, while cells expressing a relatively low level of ILK are not defective in the assembly of focal adhesion, a higher level of ILK promotes the assembly of complexes containing vinculin, $\alpha_5\beta_1$ integrin and Fn matrix.

Overexpression of ILK down-regulates E-cadherin. E-cadherin is an important epithelial cell adhesion molecule mediating cell-cell interactions. Because overexpressing ILK in epithelial cells disrupted the characteristic "cobblestone" epithelial morphology of the epithelial cells, the effect of ILK expression on the cellular level of E-cadherin was studied. The level of E-cadherin in cells expressing different amount of ILK was determined by immunoblot using an anti-E-cadherin antibody. The parental IEC-18 epithelial cells expressed abundant E-cadherin. Overexpression of H-RasVal12 in IEC-18 cells reduced the level of E-cadherin. Strikingly, E-cadherin was completely eliminated in ILK13-A1a3 and A4a cells that overexpress ILK, whereas it was present at a normal level in ILK14-A2C3 and A2C6 cells that express a similar level of ILK to the parental IEC-18 cells (FIG. 8A). These results indicate an inverse correlation between the level of ILK and that of E-cadherin.

In contrast to E-cadherin level, overexpression of ILK did not alter the ability of the cells to phosphorylate focal adhesion kinase (pp125$^{FAK}$) in response to cell adhesion to Fn, indicating that tyrosine phosphorylation of pp125$^{FAK}$ does not transduce the signals leading to the alterations observed upon ILK overexpression, and in particular tyrosine phosphorylation of pp125$^{FAK}$ does not play a regulatory role in ILK induced Fn matrix assembly Induction of in vivo tumorigenesis by overexpression of ILK. To assess a potential role of ILK in tumorigenesis, cells expressing varying levels of ILK were injected into athymic nude mice subcutaneously. Tumors arose within three weeks in 50% to 100% of the mice injected with the ILK13 cells (10$^7$ cells/mouse) that overexpress ILK, whereas no tumors were detected in the mice that were injected with the same number of the IEC-18 or ILK14 cells expressing lower levels of ILK (Table 4). Thus, overexpression of ILK in these epithelial cells promotes tumor formation in vivo.

TABLE 4

Tumorigenicity of ILK overexpressing IEC-18 Cells

| Cell Line | Number of Mice with Tumors at 3 weeks |
| --- | --- |
| IEC-18 | 0/6 |
| ILK14-A2C3 | 0/6 |
| ILK13-A1a3 | 6/6 |
| ILK13-A4a | 3/6 |

Athymic nude mice were inoculated subcutaneously with the cells expressing high (ILK13-A1a3 and A4a) or low (IEC-18 and ILK14-A2C3) levels of ILK (10$^7$ cells/mouse in PBS). The mice were monitored for tumor formation at the site of inoculation after three weeks.

Inhibition of ILK induced cell growth in soft agar by amino terminal fragments of Fn that inhibit matrix assembly. One of the hallmarks of tumor forming cells is that their growth is less dependent on anchorage as measured by their ability to grow in soft agar culture. Similar to cells overexpressing H-Ras, cells overexpressing ILK were able to grow in soft agar. However, in marked contrast to the H-Ras overexpressing cells, ILK overexpressing cells assembled an abundant Fn matrix (Table 3). It was therefore tested whether the ability of the ILK overexpressing cells to grow in soft agar culture is related to the elevated level of Fn matrix assembly. The cells overexpressing ILK and the cells overexpressing H-Ras, respectively, were cultured in soft agar either in the presence or absence of the 70 kDa Fn amino terminal fragment, which inhibits the ILK induced Fn matrix assembly. The 70 kDa Fn fragment significantly inhibited the ILK induced "anchorage independent" growth in soft agar. Similar inhibition was observed with the 29 kDa fragment of Fn. In contrast, the H-Ras induced anchorage independent growth in soft agar was not inhibited by the 70 kDa Fn fragmen. Moreover, the ILK induced cell growth in soft agar was not inhibited by the 60 kDa Fn Fragment which does not inhibit the Fn matrix assembly induced by ILK. These results suggest that the cell growth in soft agar induced by ILK, but not that induced by H-Ras, is at least partially mediated by a Fn matrix.

DISCUSSION

The overexpression of ILK results in a loss of E-cadherin protein expression, offering a possible explanation for the loss of cell-cell contact in these cells. Indeed, losses of cell-cell adhesion have been implicated in tumorigenicity in vivo. ILK overexpressing cells are tumorigenic in nude mice in contrast to the parental IEC-18 intestinal epithelial cells and the control transfected clones. Thus, ILK can be considered to be a proto-oncogene. Another important finding is the apparent involvement of ILK in Fn matrix assembly. Overexpression of ILK in IEC-18 cells stimulated Fn matrix assembly. This is a property of transfected cell clones constitutively overexpressing ILK, and also of transfected clones in which ILK expression is induced using a metallothionein inducible promoter. Furthermore, Fn matrix assembly is impaired when an anti-sense ILK cDNA is induced resulting in decreased ILK expression.

The ILK-stimulated Fn matrix assembly was inhibited by the amino-terminal domain of Fn, as well as the RGD-containing integrin binding domain of Fn, suggesting that RGD-binding integrins mediate ILK functions in Fn matrix assembly. Due to the unavailability of anti-integrin function blocking antibodies against rat integrins, it has not been possible to identify directly the specific integrin(s) involved in the enhanced Fn binding and matrix assembly. However, using immunofluorescence analysis, the $\alpha_5\beta_1$ integrin, but not $\alpha_v\beta_3$, was co-localized with Fn fibrils in the ILK overexpressing cells, implicating $\alpha_5\beta_1$ in the matrix assembly process. Furthermore, ILK overexpression promoted the co-localization of Fn with $\alpha_5\beta_1$ and vinculin, whereas in the parental IEC-18 cells and control transfected cells vinculin containing focal adhesion plaques were not co-localized with Fn.

The kinase activity of ILK is clearly important in the stimulation of Fn matrix assembly, as overexpression of a kinase-inactive ILK mutant failed to enhance Fn matrix assembly. However, because ILK has potential binding sites for integrins and probably other intracellular signaling molecules, and because Fn matrix assembly can be regulated by post ligand occupancy events, it is possible that other activities of ILK may also play important roles in the stimulation of Fn matrix assembly.

Although ILK overexpressing IEC-18 cells express same levels of integrins as the parental cells, the ILK overexpressing cells gain the ability to grow in an anchorage independent manner in soft agar, and are tumorigenic in nude mice, and they organize a prolific Fn matrix. The same IEC-18 cells transfected with an activated form of H-ras, do not assemble a Fn matrix, but nevertheless are highly tumorigenic in nude mice. This represents a novel pathway of oncogenic transformation which is distinctive from H-Ras induced transformation and involves ILK and enhanced Fn matrix assembly. In fact, the ability to form a Fn matrix is important for the anchorage independent growth of transforming growth factor β (TGF β) treated fibroblasts. Fn matrix assembly also seems to be important for anchorage-independent growth in soft agar of the ILK overexpressing cells since inhibition of matrix assembly by the 29 kDa and 70 kDa amino terminal fragments of Fn, results in an inhibition in colony formation in soft agar.

The expression of activated $p21^{ras}$ results in the disregulation of multiple signaling pathways and typically renders cells serum-independent, as well as anchorage independent for cell growth. On the other hand, the overexpression of ILK does not result in serum-independent cell growth, but induces anchorage-independent cell growth. These results indicate that ILK normally regulates adhesion-dependent signaling pathways and that the disregulation of ILK (e.g. by overexpression) induces anchorage-independent cell growth specifically. It is likely that ILK mediated signaling may be involved in the regulation of integrin inside-out signaling, as activated integrins are required for Fn matrix assembly.

The ability to assemble an extensive Fn fibrillar matrix is a property of mesenchymal cells and it is intriguing that the stimulation of this activity by ILK overexpression in the epithelial cells is accompanied by a dramatic downregulation of cellular E-cadherin expression. Numerous previous studies have established that cellular E-cadherin level or activity is downregulated during epithelial-mesenchymal transition. Moreover, in a recent study, Zuk and Hay demonstrated that inhibition of $\alpha_5\beta_1$ integrin, which is a substrate of ILK, significantly inhibited epithelial-mesenchymal transition of lens epithelium. It is now also widely accepted that many invasive carcinomas exhibit a loss of E-cadherin expression, and E-cadherin gene has been found to be a tumor/invasion-suppressor gene in human lobular breast cancer. The tumor suppressor gene fat in Drosophila is also homologous to cadherins. ILK may therefore be involved in coordinating cell-matrix adhesion and cell-cell adhesion in epithelial-mesenchymal transition, and overexpression of ILK may drive epithelial cells towards a mesenchymal phenotype and oncogenic transformation.

The ILK stimulated Fn matrix assembly may allow enhanced interaction of Fn with $\alpha_5\beta_1$. This integrin has recently been shown to be specific in supporting survival of cells on Fn, although no direct correlation was found between Fn matrix assembly and $\alpha_5\beta_1$ mediated cell survival. This latter conclusion was derived from the use of wild type $\alpha_5\beta_1$ and $\alpha_5$ cytoplasmic deleted $(\alpha_5\Delta C\beta_1)$ mutants. It is likely that for cell survival, both receptor interaction with Fn, as well as proper intracellular interactions are required. ILK overexpression in IEC-18 cells induces cell survival in suspension cultures largely due to the up-regulation of expression of cyclin $D_1$ and cyclin A proteins.

EXAMPLE 12

Expression of ILK in Human Colon Carcinoma Cells

Tumor (T) or adjacent normal (N) tissue from patients biopsied for colon carcinoma were analyzed for the expression of ILK or LEF-1 by Western blot analysis. ILK activity was further determined by an in vitro kinase assay, as described in previous examples. The data are shown in Table 5.

TABLE 5

|  | ILK Expression | | LEF-1 Expression | | ILK Activity | |
| --- | --- | --- | --- | --- | --- | --- |
| Sample # | N | T | N | T | N | T |
| 369 | + | ++ | − | − | + | + |
| 371 | ++ | ++++ | + | ++++ | + | +++ |
| 373 | ++ | ++++ | + | ++++ | + | +++ |
| 438 | − | − | − | +/− | + | ++ |
| 443 | + | ++++ | +/− | ++++ |  |  |
| 444 | +/− | ++ | +/− | ++ | ++ | ++ |
| 445 | +++ | +++ | + | + | ++ | +++ |
| 450T7W |  | ++++ |  | ++++ |  | ++ |
| 450TEW |  | ++++ |  | ++++ |  | ++ |

These data demonstrate the strong expression of ILK in colon carcinomas, indicating an association with transformation. In accordance with the data presented in the previous example, LEF-1 expression is closely tied to ILK expression.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

REFERENCES

1. Damsky C. H., and Werb Z. Curr. Opin. Cell Biol. 4, 772–781 (1992).
2. Hynes R. O. Cell 69, 11–25 (1992).
3. Clark E. A. and Brugge J. S. Science 268, 233–239 (1995).
4. Fields S. and Song O. Nature 340, 245–246 (1989).
5. Lux S. E., John K. M. and Bennett V. Nature 344, 36–42 (1990).
6. Inoue J. -l., et al. Proc. Natl. Acad. Sci. U.S.A. 89, 4333–4337 (1992).
7. Lukas J., et al. Nature 375, 503–506 (1993).
8. Schaller M. D., et al. Proc. Natl. Acad. Sci. U.S.A. 89, 5192–5196 (1992).
9. Hanks, S. K., Calalb M. B., Harper M. C. and Patel S. K. Proc. Natl. Acad. Sci. U.S.A. 89, 8481–8491 (1992).
10. Dedhar S., Saulnier R., Nagle R. and Overall C. M. Clin. Exp. Metastasis 11, 391–400 (1993).
11. Filmus J., et al., Oncogene 9, 3627–3633 (1994).
12. O'Toole T. E., et al. J. Cell Biol. 124, 1047–1059 (1994).
13. Chen Y. -P.,et al., J. Biol. Chem. 269, 18307–18310 (1994).
14. Kapron-Bras C., Fitz-Gibbon L., Jeevaratnam P., Wilkins J. and Dedhar S. J. Biol. Chem. 268, 20701–20704 (1993).
15. Chen Q., Kinch M. S., Lin T. H., Burridge K. and Juliano R. L. J. Biol. Chem. 269, 26602–26605 (1994).
16. Schlaepfer D. D., Hanks S. K., Hunter T. and van der Geer P. Nature 372, 786–791 (1994).
17. Kozak M. Cell 44, 283–292 (1986).
18. Altschul S. F., Gish W., Miller W., Myers E. W., and Lipman D. J. (1990) Basic alignment search tool. J. Mol. Biol. 215, 403–410.
19. Hanks S. K., Quinn A. M. and Hunter T. Science 241, 42–52 (1988).
20. Zervos A. S., Gyuris J. and Brent R. Cell 72, 223–232 (1993).
21. Argraves W. S.,et al. J. Cell Biol. 105,1183–1190 (1987).
22. Gietz D., St. Jean A., Woods R. A. and Schiestl R. H. Nucl. Acids Res. 20, 1425 (1992).
23. Sambrook J., Fritsch E. F. and Maniatis T. Molecular Cloning: A laboratory manual, 2nd ed. (Cold Spring Harbor Laboratory Press, New York, 1989).
24. Otey C. A., Pavalko F. M. and Burridge K. J. Cell Biol. 111, 721–729 (1990).
25. Cooper J. A., Sefton B. M. and Hunter T. Methods Enzymol. 99, 387–402 (1983).
26. Stephens L. C., Sonne J. E., Fitzgerald M. L. and Damsky C. H. J. Cell Biol. 123,1607–1620 (1993).
27. Harlow E. and Lane D. Antibodies: A Laboratory Manual. (Cold Spring Harbor Laboratory Press, New York, 1988).
28. Leung-Hagesteijn C. Y., Milankov K., Michalak M., Wilkins J. and Dedhar S. J. Cell Sci. 107, 589–600 (1994).
29. Buick, R. N., Filmus J. and Quaroni, A. Exp. Cell Res. 170, 300–309 (1987).

---

What is claimed is:

1. An isolated nucleic acid encoding a mammalian integrin-linked kinase (ILK) protein wherein said ILK protein has the amino acid sequence of SEQ ID NO:2.

2. An isolated nucleic acid wherein the nucleotide sequence of said nucleic acid comprises the sequence set forth in SEQ ID NO:1.

3. An isolated nucleic acid that will hybridize to the nucleotide sequence set forth in SEQ ID NO:1 under the following conditions: 0.1×SSC (9 mM saline/0.9 mM sodium citrate) at 50° C. or higher wherein said nucleic acid encodes a human ILK protein.

4. An expression cassette comprising a transcriptional initiation region functional in an expression host, a nucleic acid having a sequence of the isolated nucleic acid according to claim 1 under the transcriptional regulation of said transcriptional initiation region, and a transcriptional termination region functional in said expression host.

5. An isolated cell comprising an expression cassette according to claim 4 as part of an extrachromosomal element or integrated into the genome of a host cell as a result of introduction of said expression cassette into said host cell, and the cellular progeny of said host cell.

6. A method for producing mammalian ILK protein, said method comprising: growing a cell according to claim 5, whereby said mammalian ILK protein is expressed; and isolating said ILK protein free of other proteins.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1789 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
GAATTCATCT GTCGACTGCT ACCACGGGAG TTCCCCGGAG AAGGATCCTG CAGCCCGAGT      60

CCCGAGGATA AAGCTTGGGG TTCATCCTCC TTCCCTGGAT CACTCCACAG TCCTCAGGCT     120

TCCCCAATCC AGGGGACTCG GCGCCGGGAC GCTGCTATGG ACGACATTTT CACTCAGTGC     180

CGGGAGGGCA ACGCAGTCGC CGTTCGCCTG TGGCTGGACA ACACGGAGAA CGACCTCAAC     240

CAGGGGGACG ATCATGGCTT CTCCCCCTTG CACTGGGCCT GCCGAGAGGG CCGCTCTGCT     300

GTGGTTGAGA TGTTGATCAT GCGGGGGGCA CGGATCAATG TAATGAACCG TGGGGATGAC     360

ACCCCCCTGC ATCTGGCAGC CAGTCATGGA CACCGTGATA TTGTACAGAA GCTATTGCAG     420

TACAAGGCAG ACATCAATGC AGTGAATGAA CACGGGAATG TGCCCCTGCA CTATGCCTGT     480
```

```
TTTTGGGGCC AAGATCAAGT GGCAGAGGAC CTGGTGGCAA ATGGGGCCCT TGTCAGCATC      540

TGTAACAAGT ATGGAGAGAT GCCTGTGGAC AAAGCCAAGG CACCCCTGAG AGAGCTTCTC      600

CGAGAGCGGG CAGAGAAGAT GGGCCAGAAT CTCAACCGTA TTCCATACAA GGACACATTC      660

TGGAAGGGGA CCACCCGCAC TCGGCCCCGA AATGGAACCC TGAACAAACA CTCTGGCATT      720

GACTTCAAAC AGCTTAACTT CCTGACGAAG CTCAACGAGA ATCACTCTGG AGAGCTATGG      780

AAGGGCCGCT GGCAGGGCAA TGACATTGTC GTGAAGGTGC TGAAGGTTCG AGACTGGAGT      840

ACAAGGAAGA GCAGGGACTT CAATGAAGAG TGTCCCCGGC TCAGGATTTT CTCGCATCCA      900

AATGTGCTCC CAGTGCTAGG TGCCTGCCAG TCTCCACCTG CTCCTCATCC TACTCTCATC      960

ACACACTGGA TGCCGTATGG ATCCCTCTAC AATGTACTAC ATGAAGGCAC CAATTTCGTC     1020

GTGGACCAGA GCCAGGCTGT GAAGTTTGCT TTGGACATGG CAAGGGGCAT GGCCTTCCTA     1080

CACACACTAG AGCCCCTCAT CCCACGACAT GCACTCAATA GCCGTAGTGT AATGATTGAT     1140

GAGGACATGA CTGCCCGAAT TAGCATGGCT GATGTCAAGT TCTCTTTCCA ATGTCCTGGT     1200

CGCATGTATG CACCTGCCTG GGTAGCCCCC GAAGCTCTGC AGAAGAAGCC TGAAGACACA     1260

AACAGACGCT CAGCAGACAT GTGGAGTTTT GCAGTGCTTC TGTGGGAACT GGTGACACGG     1320

GAGGTACCCT TTGCTGACCT CTCCAATATG GAGATTGGAA TGAAGGTGGC ATTGGAAGGC     1380

CTTCGGCCTA CCATCCCACC AGGTATTTCC CCTCATGTGT GTAAGCTCAT GAAGATCTGC     1440

ATGAATGAAG ACCCTGCAAA GCGACCCAAA TTTGACATGA TTGTGCCTAT CCTTGAGAAG     1500

ATGCAGGACA AGTAGGACTG GAAGGTCCTT GCCTGAACTC CAGAGGTGTC GGGACATGGT     1560

TGGGGGAATG CACCTCCCCA AAGCAGCAGG CCTCTGGTTG CCTCCCCCGC CTCCAGTCAT     1620

GGTACTACCC CAGCCTGGGG TCCATCCCCT TCCCCCATCC CTACCACTGT GCGCAAGAGG     1680

GGCGGGCTCA GAGCTTTGTC ACTTGCCACA TGGTGTCTCC CAACATGGGA GGGATCAGCC     1740

CCGCCTGTCA CAATAAAGTT TATTATGAAA AAAAAAAAA AAAAAAAA                   1789

(2) INFORMATION FOR SEQ ID NO:2:

(i) SEQUENCE CHARACTERISTICS:
        (A) LENGTH: 452 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Asp Asp Ile Phe Thr Gln Cys Arg Glu Gly Asn Ala Val Ala Val
1               5                  10                  15

Arg Leu Trp Leu Asp Asn Thr Glu Asn Asp Leu Asn Gln Gly Asp Asp
            20                  25                  30

His Gly Phe Ser Pro Leu His Trp Ala Cys Arg Glu Gly Arg Ser Ala
        35                  40                  45

Val Val Glu Met Leu Ile Met Arg Gly Ala Arg Ile Asn Val Met Asn
    50                  55                  60

Arg Gly Asp Asp Thr Pro Leu His Leu Ala Ala Ser His Gly His Arg
65                  70                  75                  80

Asp Ile Val Gln Lys Leu Leu Gln Tyr Lys Ala Asp Ile Asn Ala Val
                85                  90                  95

Asn Glu His Gly Asn Val Pro Leu His Tyr Ala Cys Phe Trp Gly Gln
            100                 105                 110

Asp Gln Val Ala Glu Asp Leu Val Ala Asn Gly Ala Leu Val Ser Ile
```

-continued

```
            115                 120                 125
Cys Asn Lys Tyr Gly Glu Met Pro Val Asp Lys Ala Lys Ala Pro Leu
    130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Arg Thr Arg
                165                 170                 175

Pro Arg Asn Gly Thr Leu Asn Lys His Ser Gly Ile Asp Phe Lys Gln
                180                 185                 190

Leu Asn Phe Leu Thr Lys Leu Asn Glu Asn His Ser Gly Glu Leu Trp
                195                 200                 205

Lys Gly Arg Trp Gln Gly Asn Asp Ile Val Val Lys Val Leu Lys Val
    210                 215                 220

Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
                245                 250                 255

Cys Gln Ser Pro Pro Ala Pro His Pro Thr Leu Ile Thr His Trp Met
        260                 265                 270

Pro Tyr Gly Ser Leu Tyr Asn Val Leu His Glu Gly Thr Asn Phe Val
        275                 280                 285

Val Asp Gln Ser Gln Ala Val Lys Phe Ala Leu Asp Met Ala Arg Gly
290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
                340                 345                 350

Pro Ala Trp Val Ala Pro Glu Ala Leu Gln Lys Lys Pro Glu Asp Thr
        355                 360                 365

Asn Arg Arg Ser Ala Asp Met Trp Ser Phe Ala Val Leu Leu Trp Glu
        370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Pro Thr Ile Pro Pro Gly
                405                 410                 415

Ile Ser Pro His Val Cys Lys Leu Met Lys Ile Cys Met Asn Glu Asp
                420                 425                 430

Pro Ala Lys Arg Pro Lys Phe Asp Met Ile Val Pro Ile Leu Glu Lys
        435                 440                 445

Met Gln Asp Lys
    450
```

(2) INFORMATION FOR SEQ ID NO:3:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Asn Met Lys Glu Leu Lys Leu Leu Gln Thr Ile Gly Lys Gly Glu Phe
1               5                   10                  15
```

```
Gly Asp Val Met Leu Gly Asp Tyr Arg Gly Asn Lys Val Ala Val Lys
             20                  25                  30

Cys Ile Lys Asn Asp Ala Thr Ala Gln Ala Phe Leu Ala Glu Ala Ser
             35                  40                  45

Val Met Thr Gln Leu Arg His Ser Asn Leu Val Gln Leu Leu Gly Val
 50                      55                  60

Ile Val Glu Glu Lys Gly Gly Leu Tyr Ile Val Thr Glu Tyr Met Ala
 65                      70                  75                  80

Lys Gly Ser Leu Val Asp Tyr Leu Arg Ser Arg Gly Arg Ser Val Leu
                     85                  90                  95

Gly Gly Asp Cys Leu Leu Lys Phe Ser Leu Asp Val Cys Glu Ala Met
                 100                 105                 110

Glu Tyr Leu Glu Gly Asn Asn Phe Val His Arg Asp Leu Ala Ala Arg
             115                 120                 125

Asn Val Leu Val Ser Glu Asp Asn Val Ala Lys Val Ser Asp Phe Gly
 130                     135                 140

Leu Thr Lys Glu Ala Ser Ser Thr Gln Asp Thr Gly Lys Leu Pro Val
145                      150                 155                 160

Lys Trp Thr Ala Pro Glu Ala Leu Arg Glu Lys Lys Phe Ser Thr Lys
                 165                 170                 175

Ser Asp Val Trp Ser Phe Gly Ile Leu Leu Trp Glu Ile Tyr Ser Phe
                 180                 185                 190

Gly Arg Val Pro Tyr Pro Arg Ile Pro Leu Lys Asp Val Val Pro Arg
                 195                 200                 205

Val Glu Lys Gly Tyr Lys Met Asp Ala Pro Asp Gly Cys Pro Pro Ala
 210                     215                 220

Val Tyr Glu Val Met Lys Asn Cys Trp His Leu Asp Ala Ala Met Arg
225                      230                 235                 240

Pro Ser Phe Leu Gln Leu Arg Glu Gln Leu Glu His Ile Lys Thr His
                 245                 250                 255

Glu Leu (2) INFORMATION FOR SEQ ID NO:4:

(i) SEQUENCE CHARACTERISTICS:
        (A) LENGTH: 256 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ile Pro Arg Glu Ser Leu Arg Leu Glu Val Lys Leu Gly Gln Gly Cys
 1                    5                  10                  15

Phe Gly Glu Val Trp Met Gly Thr Trp Asn Gly Thr Thr Lys Val Ala
             20                  25                  30

Ile Lys Thr Leu Lys Pro Gly Thr Met Met Pro Glu Ala Phe Leu Gln
             35                  40                  45

Glu Ala Gln Ile Met Lys Lys Leu Arg His Asp Lys Leu Val Pro Leu
 50                      55                  60

Tyr Ala Val Val Ser Glu Pro Ile Tyr Ile Val Thr Glu Phe Met
 65                      70                  75                  80

Thr Lys Gly Ser Leu Leu Asp Phe Leu Lys Glu Gly Glu Gly Lys Phe
                     85                  90                  95

Leu Lys Leu Pro Gln Leu Val Asp Met Ala Ala Gln Ile Ala Asp Gly
```

```
            100                 105                 110
Met Ala Tyr Ile Glu Arg Met Asn Tyr Ile His Arg Asp Leu Arg Ala
            115                 120                 125

Ala Asn Ile Leu Val Gly Asp Asn Leu Val Cys Lys Ile Ala Asp Phe
            130                 135                 140

Gly Leu Ala Arg Leu Ile Glu Asp Asn Glu Tyr Thr Ala Arg Gln Gly
145                 150                 155                 160

Ala Lys Phe Pro Ile Lys Trp Thr Ala Pro Glu Ala Leu Tyr Gly
                165                 170                 175

Arg Phe Thr Ile Lys Ser Asp Val Trp Ser Phe Gly Ile Leu Leu Thr
            180                 185                 190

Glu Leu Val Thr Lys Gly Arg Val Pro Tyr Pro Gly Met Val Asn Arg
            195                 200                 205

Glu Val Leu Glu Gln Val Glu Arg Gly Tyr Arg Met Pro Cys Pro Gln
            210                 215                 220

Gly Cys Pro Glu Ser Leu His Glu Leu Met Lys Leu Cys Trp Lys Lys
225                 230                 235                 240

Asp Pro Asp Glu Arg Pro Thr Phe Glu Tyr Ile Gln Ser Phe Leu Glu
                245                 250                 255

(2) INFORMATION FOR SEQ ID NO:5:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ile Pro Trp Cys Asp Leu Asn Ile Lys Glu Lys Ile Gly Ala Gly Ser
1                   5                   10                  15

Phe Gly Thr Val His Arg Ala Glu Trp His Gly Ser Asp Val Ala Val
            20                  25                  30

Lys Ile Leu Met Glu Gln Asp Phe His Ala Glu Arg Val Asn Glu Phe
            35                  40                  45

Leu Arg Glu Val Ala Ile Met Lys Arg Leu Arg His Pro Asn Ile Val
50                  55                  60

Leu Phe Met Gly Ala Val Thr Gln Pro Pro Asn Leu Ser Ile Val Thr
65                  70                  75                  80

Glu Tyr Leu Ser Arg Gly Ser Leu Tyr Arg Leu Leu His Lys Ser Gly
            85                  90                  95

Ala Arg Glu Gln Leu Asp Glu Arg Arg Leu Ser Met Ala Tyr Asp
            100                 105                 110

Val Ala Lys Gly Met Asn Tyr Leu His Asn Arg Asn Pro Pro Ile Val
            115                 120                 125

His Arg Asp Leu Lys Ser Pro Asn Leu Leu Val Asp Lys Lys Tyr Thr
            130                 135                 140

Val Lys Val Cys Asp Phe Gly Leu Ser Arg Leu Lys Ala Ser Thr Phe
145                 150                 155                 160

Leu Ser Ser Lys Ser Ala Ala Gly Thr Pro Glu Trp Met Ala Pro Glu
                165                 170                 175

Val Leu Arg Asp Glu Pro Ser Asn Glu Lys Ser Asp Val Tyr Ser Phe
            180                 185                 190

Gly Val Ile Leu Trp Glu Leu Ala Thr Leu Gln Gln Pro Trp Gly Asn
            195                 200                 205
```

Leu Asn Pro Ala Gln Val Val Ala Ala Val Gly Phe Lys Cys Lys Arg
        210             215                 220

Leu Glu Ile Pro Arg Asn Leu Asn Pro Gln Val Ala Ala Ile Ile Glu
225                 230                 235                 240

Gly Cys Trp Thr Asn Glu Pro Trp Lys Arg Pro Ser Phe Ala Thr Ile
                245                 250                 255

Met Asp Leu Leu Arg Pro Leu
            260

(2) INFORMATION FOR SEQ ID NO:6:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ile Pro Asp Gly Gln Ile Thr Val Gly Gln Arg Ile Gly Ser Gly Ser
1               5                   10                  15

Phe Gly Thr Val Tyr Lys Gly Lys Trp His Gly Asp Val Ala Val Lys
            20                  25                  30

Met Leu Asn Val Thr Ala Pro Thr Pro Gln Gln Leu Gln Ala Phe Lys
        35                  40                  45

Asn Glu Val Gly Val Leu Arg Lys Thr Arg His Val Asn Ile Leu Leu
    50                  55                  60

Phe Met Gly Tyr Ser Thr Lys Pro Gln Leu Ala Ile Val Thr Gln Trp
65                  70                  75                  80

Cys Glu Gly Ser Ser Leu Tyr His His Leu His Ile Ile Glu Thr Lys
                85                  90                  95

Phe Glu Met Ile Lys Leu Ile Asp Ile Ala Arg Gln Thr Ala Gln Gly
            100                 105                 110

Met Asp Tyr Leu His Ala Lys Ser Ile Ile His Arg Asp Leu Lys Ser
        115                 120                 125

Asn Asn Ile Phe Leu His Glu Asp Leu Thr Val Lys Ile Gly Asp Phe
    130                 135                 140

Gly Leu Ala Thr Val Lys Ser Arg Trp Ser Gly Ser His Gln Phe Glu
145                 150                 155                 160

Gln Leu Ser Gly Ser Ile Leu Trp Met Ala Pro Glu Val Ile Arg Met
                165                 170                 175

Gln Asp Lys Asn Pro Tyr Ser Phe Gln Ser Asp Val Tyr Ala Phe Gly
            180                 185                 190

Ile Val Leu Tyr Glu Leu Met Thr Gly Gln Leu Pro Tyr Ser Asn Ile
        195                 200                 205

Asn Asn Arg Asp Gln Ile Ile Phe Met Val Gly Arg Gly Tyr Leu Ser
    210                 215                 220

Pro Asp Leu Ser Lys Val Arg Ser Asn Cys Pro Lys Ala Met Lys Arg
225                 230                 235                 240

Leu Met Ala Glu Cys Leu Lys Lys Lys Arg Asp Glu Arg Pro Leu Phe
                245                 250                 255

Pro Gln Ile Leu Ala Ser Ile Glu Leu Leu Ala Arg Ser Leu Pro
            260                 265                 270

(2) INFORMATION FOR SEQ ID NO:7:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:7:

GGCCGAATTC GCTGGAATTG TTCTTATTGG C          31

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

GGCCGGATCC TCATTTTCCC TCATACTTCG G          31

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

CCTTCAGCAC CCTCACGACA ATGTCATTGC CC         32

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

CTGCAGAGCT TTGGGGGCAT CCCAGGCAGG TG         32

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Leu Pro Tyr Gly Thr Ala Met Glu Lys Ala Gln Leu Lys Pro Pro Ala
 1               5                  10                  15

Thr Ser Asp Ala
            20